(12) United States Patent
Gao et al.

(10) Patent No.: US 10,263,746 B2
(45) Date of Patent: Apr. 16, 2019

(54) METHODS AND SYSTEMS FOR CSI-RS PORT SELECTION FOR CSI-REPORTING

(71) Applicant: Telefonaktiebolaget LM Ericsson (publ), Stockholm (SE)

(72) Inventors: Shiwei Gao, Nepean (CA); Mattias Frenne, Uppsala (SE); Robert Mark Harrison, Grapevine, TX (US); Siva Muruganathan, Stittsville (CA)

(73) Assignee: Telefonaktiebolaget LM Ericsson (publ), Stockholm (SE)

( * ) Notice: Subject to any disclaimer, the term of this patent is extended or adjusted under 35 U.S.C. 154(b) by 0 days.

(21) Appl. No.: 15/032,648

(22) PCT Filed: Mar. 23, 2016

(86) PCT No.: PCT/SE2016/050241
§ 371 (c)(1),
(2) Date: Apr. 28, 2016

(87) PCT Pub. No.: WO2017/078588
PCT Pub. Date: May 11, 2017

(65) Prior Publication Data
US 2017/0264405 A1    Sep. 14, 2017

Related U.S. Application Data

(60) Provisional application No. 62/251,574, filed on Nov. 5, 2015.

(51) Int. Cl.
*H04L 5/00* (2006.01)
*H04B 7/04* (2017.01)
(Continued)

(52) U.S. Cl.
CPC ............ *H04L 5/0048* (2013.01); *H04B 7/04* (2013.01); *H04B 7/0417* (2013.01); *H04B 7/0626* (2013.01)

(58) Field of Classification Search
CPC ... H04L 5/0048; H04L 1/0023; H04B 7/0626; H04B 7/0417; H04B 7/02; H04B 10/532; H04B 7/0413; H04B 7/15571
See application file for complete search history.

(56) References Cited

U.S. PATENT DOCUMENTS

2016/0157218 A1* 6/2016 Nam ................... H04B 7/0456
                                                         370/329
2017/0134130 A1* 5/2017 Li ......................... H04L 5/0048

OTHER PUBLICATIONS

Source: Intel Corporation Title: "On the need of the flexible CSI-RS configuration for non precoded CSI-RS" 3GPP TSG RAN WG1 Meeting #82bis Agenda item: 7.2.4.2.1.*

(Continued)

*Primary Examiner* — Andrew Lai
*Assistant Examiner* — Harry H Kim
(74) *Attorney, Agent, or Firm* — Baker Botts, LLP

(57) ABSTRACT

According to certain embodiments, a method in a network node is disclosed. The method comprises selecting a subset from a predetermined set of P CSI-RS ports for receiving channel information. The network node comprises an antenna array with controllable polarization. Each CSI-RS port corresponds to a combination of a set of resource elements and an antenna port of said antenna array. The predetermined set comprises a first number $P_1$ of CSI-RS ports with a first polarization state and a second number $P_2$ of CSI-RS ports with a second polarization state. The first and second polarization states are distinct. The method further comprises populating the subset with Q CSI-RS ports in such manner that the ratio of CSI-RS ports respectively having the first and second polarization states is equal to the ratio of the first and second numbers.

24 Claims, 24 Drawing Sheets

(51) Int. Cl.
H04B 7/06 (2006.01)
H04B 7/0417 (2017.01)

(56) References Cited

OTHER PUBLICATIONS

Intel Corporation, On the need of the flexible CSI_RS configuration for non precoded CSI-RS, Oct. 9, 2015, 3GPP TSG RAN WG1, Meeting #82bis (Year: 2015).*
3GPP TSG RAN WG1 Meeting #82, Aug. 2015, ZTE "Discussion on CSI Process and CSI-RS Resource Definitions".*
3GPP TSG RAN WG1 Meeting #82bis, Oct. 2015, Intel Corporation "On the need of the flexible CSI-Rs configuration for non-precoded CSI-RS", 7.2.4.2.1.*
3GPP TSG RAN WG #82bis, Malmo, Sweden, Oct. 2015, Ericsson "Configuration of FD-MIMO" 7.2.4.1.*
3GPP TSG-RAN WG1 #82bis, Malmo, Sweden, Oct. 2015, Ericsson "On CSI feedback for FD-MIMO" 7.2.4.3.3.*
3GPP TS 36.211 v12.5.0; Technical Specification; 3rd Generation Partnership Project; Technical Specification Group Radio Access Network; Evolved Universal Terrestrial Radio Access (E-UTRA); Physical channels and modulation (Release 12).

PCT Invitation to Pay Additional Fees and, Where Applicable, Protest Fee for International application No. PCT/SE2016/050241—dated Jul. 19, 2016.
3GPP TSG RAN WG1 Meeting #82bis; Malmö, Sweden; Source: Intel Corporation; Title: On the need of the flexible CSI-RS configuration for non precoded CSI-RS (R1-155318)—Oct. 5-9, 2015.
3GPP TSG RAN WG1 Meeting #82; Beijing, China; Source: ZTE; Title: Discussion on CSI Process and CSI-RS Resource Definitions (R1-154378)—Aug. 24-28, 2015.
PCT Notification of Transmittal of the International Preliminary Report on Patentability for International application No. PCT/SE2016/050241—dated Feb. 22, 2018.
PCT International Preliminary Report on Patentability for International application No. PCT/SE2016/050241—dated Feb. 22, 2018.
3GPP TSG RAN WG1 Meeting #82; Beijing, China; Title: Antenna configurations and antenna port numbering for FD-MIMO; Source: Samsung (R1-154157)—Aug. 24-28, 2015.
Communication Pursuant to Article 94(3) EPC issued for Application No. 16 718 738.4-1220—dated Sep. 14, 2018.
3GPP TSG-RAN WG1 #82bis; Malmo, Sweden; Source; Ericsson; Title: Configuration of FD-MIMO (R1-155673)—Oct. 5-9, 2015.
3GPP TSG-RAN WG1 #82bis; Malmo, Sweden; Source: Ericsson; Title: on CSI feedback for FD-MIMO (R1-155682)—Oct. 5-19, 2015.

* cited by examiner

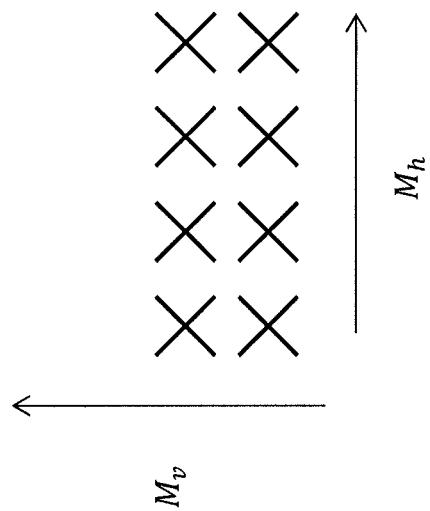
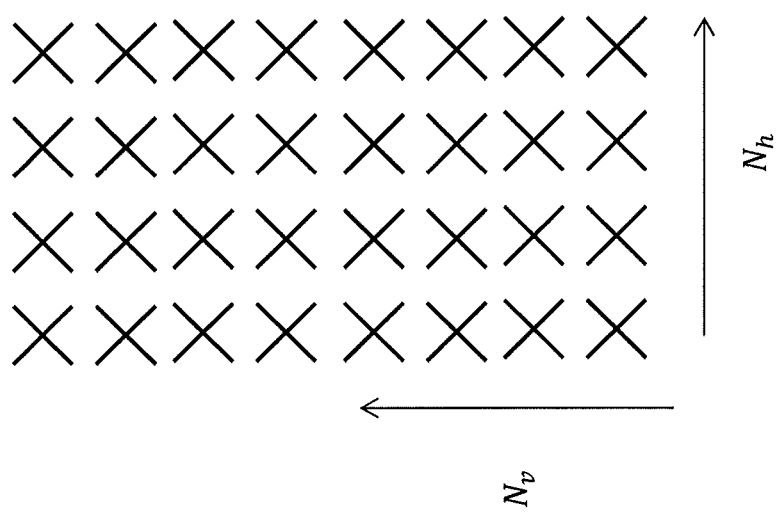
FIGURE 7

METHODS AND SYSTEMS FOR CSI-RS PORT SELECTION FOR CSI-REPORTING

PRIORITY

This nonprovisional application is a U.S. National Stage Filing under 35 U.S.C. § 371 of International Patent Application Serial No. PCT/SE2016/050241 filed Mar. 23, 2016, and entitled "Methods And Systems For CSI-RS Port Selection For CSI-Reporting" which claims priority to U.S. Provisional Patent Application No. 62/251,574 filed Nov. 5, 2015, both of which are hereby incorporated by reference in their entirety.

TECHNICAL FIELD

The present disclosure relates, in general, to wireless communications and, more particularly, to CSI-RS port to resource mapping and selection of a subset of CSI-RS ports for CSI reporting.

BACKGROUND

FIG. 1 illustrates the basic Long Term Evolution (LTE) downlink physical resource. LTE uses Orthogonal Frequency Division Multiplexing (OFDM) in the downlink and Discrete Fourier Transform (DFT)-spread OFDM in the uplink. The basic LTE downlink physical resource can thus be seen as a time-frequency grid, where each resource element (or time/frequency resource element, TFRE) corresponds to one OFDM subcarrier during one OFDM symbol interval.

FIG. 2 illustrates the LTE time-domain structure. In the time domain, LTE downlink transmissions are organized into radio frames of 10 ms. Each radio frame consists of ten equally-sized subframes of length $T_{subframe}=1$ ms.

Furthermore, the resource allocation in LTE is typically described in terms of resource blocks (RBs), where a resource block corresponds to one slot (0.5 ms) in the time domain and 12 contiguous subcarriers in the frequency domain. Resource blocks are numbered in the frequency domain, starting with 0 from one end of the system bandwidth.

FIG. 3 illustrates an example downlink subframe. Downlink transmissions are dynamically scheduled. In other words, in each subframe the base station transmits control information about to which terminals data is transmitted and upon which resource blocks the data is transmitted in the current downlink subframe. This control signaling is typically transmitted in the first 1, 2, 3 or 4 OFDM symbols in each subframe. For example, FIG. 3 illustrates a downlink system with 3 OFDM symbols as control.

LTE uses hybrid-ARQ, where, after receiving downlink data in a subframe, the terminal attempts to decode it and reports to the base station whether the decoding was successful. If the decoding is successful, the terminal reports an acknowledgement (ACK) to the base station. Conversely, if the decoding is not successful, the terminal reports an negative acknowledgement (NAK) to the base station. In case of an unsuccessful decoding attempt, the base station can retransmit the erroneous data.

Uplink control signaling from the terminal to the base station includes hybrid-ARQ acknowledgements for received downlink data. Uplink control signaling may also include terminal reports related to the downlink channel conditions, used as assistance for the downlink scheduling. Additionally, uplink control signaling may include scheduling requests, indicating that a mobile terminal needs uplink resources for uplink data transmissions. If the mobile terminal has not been assigned an uplink resource for data transmission, the L1/L2 control information (Layer-1/Layer-2 control information, e.g., channel state information (CSI) reports, hybrid-ARQ acknowledgments, and scheduling requests) is transmitted in uplink resources (resource blocks) specifically assigned for uplink L1/L2 control on the Physical Uplink Control Channel (PUCCH).

FIG. 4 illustrates uplink L1/L2 control signaling transmission on PUCCH. The uplink resources assigned for uplink L1/L2 control on the PUCCH are located at the edges of the total available cell bandwidth. Each such resource consists of twelve subcarriers (one resource block) within each of the two slots of an uplink subframe. In order to provide frequency diversity, these frequency resources are frequency hopping on the slot boundary (i.e., one "resource" consists of 12 subcarriers at the upper part of the spectrum within the first slot of a subframe and an equally sized resource at the lower part of the spectrum during the second slot of the subframe or vice versa). If more resources are needed for the uplink L1/L2 control signaling, for example in the case of very large overall transmission bandwidth supporting a large number of users, additional resource blocks can be assigned next to the previously assigned resource blocks.

As described above, uplink L1/L2 control signaling includes hybrid-ARQ acknowledgements, channel state information reports and scheduling requests. Different combinations of these types of messages are possible as described below, but to explain the structure for these cases it is beneficial to discuss separate transmission of each of the types first, starting with the hybrid-ARQ and the scheduling request. There are three formats defined for PUCCH, each capable of carrying a different number of bits. A brief description of PUCCH format 2 is provided below.

In PUCCH format 2, channel state information reports are used to provide the eNodeB with an estimate of the channel properties at the terminal in order to aid channel-dependent scheduling. A channel state information report consists of multiple bits per subframe. PUCCH format 1, which is capable of at most two bits of information per subframe, may not be suitable for this purpose. Transmission of channel state information reports on the PUCCH is instead handled by PUCCH format 2, which is capable of multiple information bits per subframe. There are three variants in the LTE specifications: formats 2; 2a; and 2b. Formats 2a and 2b are used for simultaneous transmission of hybrid-ARQ acknowledgements (described in more detail below). For simplicity, they may all referred to as format 2 herein. The PUCCH format 2 resources are semi-statically configured.

Multi-antenna techniques can significantly increase the data rates and reliability of a wireless communication system. The performance is in particular improved if both the transmitter and the receiver are equipped with multiple antennas, which results in a multiple-input multiple-output (MIMO) communication channel. Such systems and/or related techniques are commonly referred to as MIMO.

The LTE standard is currently evolving with enhanced MIMO support. A core component in LTE is the support of MIMO antenna deployments and MIMO related techniques. LTE-Advanced supports an 8-layer spatial multiplexing mode for 8 transmit (Tx) antennas with channel dependent precoding. The spatial multiplexing mode is aimed for high data rates in favorable channel conditions.

FIG. 5 illustrates an example of spatial multiplexing operation. More particularly, FIG. 5 illustrates an example transmission structure of precoded spatial multiplexing mode in LTE. As depicted, the information carrying symbol vector s is multiplied by an $N_T \times r$ precoder matrix W, which serves to distribute the transmit energy in a subspace of the $N_T$ (corresponding to $N_T$ antenna ports) dimensional vector space. The precoder matrix is typically selected from a codebook of possible precoder matrices, and typically indicated by means of a precoder matrix indicator (PMI), which specifies a unique precoder matrix in the codebook for a given number of symbol streams. The r symbols in s each correspond to a layer and r is referred to as the transmission rank. In this way, spatial multiplexing is achieved since multiple symbols can be transmitted simultaneously over the same time/frequency resource element (TFRE). The number of symbols r is typically adapted to suit the current channel properties.

LTE uses OFDM in the downlink (and DFT precoded OFDM in the uplink) and hence the received $N_R \times 1$ vector $y_n$ over $N_R$ receiving antenna ports for a certain TFRE on subcarrier n (or alternatively data TFRE number n) is thus modeled by:

$$y_n = H_n W s_n + e_n$$

where $H_n$ is the channel matrix between eNodeB and a UE, W is the precoding matrix, $s_n$ is the transmitted symbol vector, and $e_n$ is a noise/interference vector obtained as realizations of a random process. The precoder, W, can be a wideband precoder, which is constant over frequency, or frequency selective (i.e., different precoders on different subbands).

The precoder matrix is often chosen to match the characteristics of the $N_R \times N_T$ MIMO channel matrix $H_n$, resulting in so-called channel dependent precoding. This is also commonly referred to as closed-loop precoding, and essentially strives for focusing the transmit energy into a subspace which is strong in the sense of conveying much of the transmitted energy to the UE. In addition, the precoder matrix may also be selected to strive for orthogonalizing the channel, meaning that after proper linear equalization at the UE, the inter-layer interference is reduced.

The transmission rank, and thus the number of spatially multiplexed layers, is reflected in the number of columns of the precoder. For efficient performance, it is important that a transmission rank that matches the channel properties is selected.

In LTE Release 10, a new reference symbol sequence was introduced for estimating channel state information, the Channel State Information Reference Signal (CSI-RS). The CSI-RS provides several advantages over basing the CSI feedback on the cell specific reference signals (CRS), which were used for that purpose in previous releases. First, the CSI-RS is not used for demodulation of the data signal, and thus does not require the same density (i.e., the overhead of the CSI-RS is substantially less). Second, CSI-RS provides a much more flexible means to configure CSI feedback measurements (e.g., which CSI-RS resource to measure on can be configured in a UE specific manner).

By measuring on a CSI-RS, a UE can estimate the effective channel the CSI-RS is traversing (including the radio propagation channel and antenna gains). This implies that if a known CSI-RS signal X is transmitted, a UE can estimate the coupling between the transmitted signal and the received signal (i.e., the effective channel). Hence if no virtualization is performed in the transmission, the received signal y can be expressed as:

$$y = Hx + e$$

and the UE can estimate the effective channel H.

Up to eight CSI-RS ports can be configured for a Release 11 UE. That is, the UE can thus estimate the channel from up to eight transmit antennas.

FIGS. 6A-6C illustrate resource element grids. More particularly, FIGS. 6A-6C illustrate resource element grids over an RB pair showing potential positions for Release 9/10 UE specific RS, CSI-RS (marked with a number corresponding to the CSI-RS antenna port), and CRS. The CSI-RS utilizes an orthogonal cover code (OCC) of length two to overlay two antenna ports on two consecutive REs. As shown in FIGS. 6A-6C, many different CSI-RS patterns are available. For the case of 2 CSI-RS antenna ports, we see that there are 20 different patterns within a subframe. The corresponding number of patterns is 10 and 5 for 4 and 8 CSI-RS antenna ports, respectively. For TDD, some additional CSI-RS patterns are available.

The CSI reference signal configurations are shown in TABLE 6.10.5.2-1 below, taken from TS 36.211 v.12.5.0. For example, the CSI RS configuration 5 for 4 antennas ports use (k',l')=(9,5) in slot 1 (the second slot of the subframe). Using the formulas below, it can be determined that port 15,16, use OCC over the resource elements (k,l)= (9,5), (9,6) and ports 17,18 use OCC over resource elements (3,5), (3,6), respectively (assuming PRB index m=0), where k is the subcarrier index and l is the OFDM symbol index within each slot.

The orthogonal cover code (OCC) is introduced below by the factor $w_{l''}$.

$$k = k' + 12m + \begin{cases} -0 & \text{for } p \in \{15, 16\}, \text{ normal cyclic prefix} \\ -6 & \text{for } p \in \{17, 18\}, \text{ normal cyclic prefix} \\ -1 & \text{for } p \in \{19, 20\}, \text{ normal cyclic prefix} \\ -7 & \text{for } p \in \{21, 22\}, \text{ normal cyclic prefix} \\ -0 & \text{for } p \in \{15, 16\}, \text{ extended cyclic prefix} \\ -3 & \text{for } p \in \{17, 18\}, \text{ extended cyclic prefix} \\ -6 & \text{for } p \in \{19, 20\}, \text{ extended cyclic prefix} \\ -9 & \text{for } p \in \{21, 22\}, \text{ extended cyclic prefix} \end{cases}$$

$$l = l' + \begin{cases} l'' & \text{CSI reference signal configurations 0-19, normal cyclic prefix} \\ 2l'' & \text{CSI reference signal configurations 20-31, normal cyclic prefix} \\ l'' & \text{CSI reference signal configurations 0-27, extended cyclic prefix} \end{cases}$$

$$w_{l''} = \begin{cases} 1 & p \in \{15, 17, 19, 21\} \\ (-1)^{l''} & p \in \{16, 18, 20, 22\} \end{cases}$$

$$l'' = 0, 1$$

$$m = 0, 1, \ldots, N_{RB}^{DL} - 1$$

$$m' = m + \left\lfloor \frac{N_{RB}^{max,DL} - N_{RB}^{DL}}{2} \right\rfloor$$

TABLE 6.10.5.2-1

Mapping from CSI reference signal configuration to (k', l') for normal cyclic prefix.

| | CSI reference signal configuration | Number of CSI reference signals configured | | | | | |
|---|---|---|---|---|---|---|---|
| | | 1 or 2 | | 4 | | 8 | |
| | | (k', l') | $n_s$ mod 2 | (k', l') | $n_s$ mod 2 | (k', l') | $n_s$ mod 2 |
| Frame structure type 1 and 2 | 0 | (9, 5) | 0 | (9, 5) | 0 | (9, 5) | 0 |
| | 1 | (11, 2) | 1 | (11, 2) | 1 | (11, 2) | 1 |
| | 2 | (9, 2) | 1 | (9, 2) | 1 | (9, 2) | 1 |
| | 3 | (7, 2) | 1 | (7, 2) | 1 | (7, 2) | 1 |
| | 4 | (9, 5) | 1 | (9, 5) | 1 | (9, 5) | 1 |
| | 5 | (8, 5) | 0 | (8, 5) | 0 | | |
| | 6 | (10, 2) | 1 | (10, 2) | 1 | | |
| | 7 | (8, 2) | 1 | (8, 2) | 1 | | |
| | 8 | (6, 2) | 1 | (6, 2) | 1 | | |
| | 9 | (8, 5) | 1 | (8, 5) | 1 | | |
| | 10 | (3, 5) | 0 | | | | |
| | 11 | (2, 5) | 0 | | | | |
| | 12 | (5, 2) | 1 | | | | |
| | 13 | (4, 2) | 1 | | | | |
| | 14 | (3, 2) | 1 | | | | |
| | 15 | (2, 2) | 1 | | | | |
| | 16 | (1, 2) | 1 | | | | |
| | 17 | (0, 2) | 1 | | | | |
| | 18 | (3, 5) | 1 | | | | |
| | 19 | (2, 5) | 1 | | | | |
| Frame structure type 2 only | 20 | (11, 1) | 1 | (11, 1) | 1 | (11, 1) | 1 |
| | 21 | (9, 1) | 1 | (9, 1) | 1 | (9, 1) | 1 |
| | 22 | (7, 1) | 1 | (7, 1) | 1 | (7, 1) | 1 |
| | 23 | (10, 1) | 1 | (10, 1) | 1 | | |
| | 24 | (8, 1) | 1 | (8, 1) | 1 | | |
| | 25 | (6, 1) | 1 | (6, 1) | 1 | | |
| | 26 | (5, 1) | 1 | | | | |
| | 27 | (4, 1) | 1 | | | | |
| | 28 | (3, 1) | 1 | | | | |
| | 29 | (2, 1) | 1 | | | | |
| | 30 | (1, 1) | 1 | | | | |
| | 31 | (0, 1) | 1 | | | | |

For CSI feedback, LTE has adopted an implicit CSI mechanism where a UE does not explicitly report, for example, the complex valued elements of a measured effective channel, but rather the UE recommends a transmission configuration for the measured effective channel. Thus, the recommended transmission configuration implicitly gives information about the underlying channel state.

In LTE, the CSI feedback is given in terms of a transmission rank indicator (RI), a precoder matrix indicator (PMI), and one or two channel quality indicators (CQIs). The CQI/RI/PMI report can be wideband or frequency selective depending on which reporting mode is configured. The RI corresponds to a recommended number of streams that are to be spatially multiplexed and thus transmitted in parallel over the effective channel. The PMI identifies a recommended precoder (in a codebook which contains precoders with the same number of rows as the number of CSI-RS ports) for the transmission, which relates to the spatial characteristics of the effective channel. The CQI represents a recommended transport block size (i.e., code rate) and LTE supports one or two simultaneous (on different layers) transmissions of transport blocks (i.e., separately encoded blocks of information) to a UE in a subframe. There is thus a relation between a CQI and an SINR of the spatial stream(s) over which the transport block or blocks are transmitted.

In LTE Release 10, CSI feedback can correspond to multiple downlink carriers, in which case CSI feedback such as CQI/PMI/RI can be provided for each serving cell corresponding to each of the downlink carriers. In this context, P antenna ports of an antenna configuration of a network node are present on the same serving cell, and a CQI/PMI/RI report for P antenna ports for the cell corresponds to the P antenna ports present on the serving cell.

In LTE Release 11, CSI processes are defined such that each CSI process is associated with a CSI-RS resource and a CSI interference measurement (CSI-IM) resource. A UE in transmission mode 10 can be configured with one or more (up to four) CSI processes per serving cell by higher layers, and each CSI reported by the UE corresponds to a CSI process. A UE may be configured with a RI-reference CSI process for any CSI process, such that the reported RI for the CSI process is the same as for the RI-reference CSI process. This configuration may be used to force a UE to report the same RI for several different interference hypotheses, even though another RI would be the best choice for some hypothesis. Furthermore, a UE is restricted to report PMI and RI within a precoder codebook subset configured for each CSI process by higher layer signaling. This configuration may also be used to force a UE to report a specific rank for a certain CSI process.

Both aperiodic (i.e., triggered by eNB) and periodic CSI reports are supported (known as PA-CSI and P-CSI, respectively). CSI reports are also referred to as CSI feedback, and these terms may be used interchangeably herein. In the CSI process, a set of CSI-RS ports are configured for which the UE performs measurements. These CSI-RS ports are configured to be periodically transmitted with, for example, 5 ms, 10 ms, 20 ms, or any other suitable periodicity. The periodic CSI report uses PUCCH format 2 (or its variants 2a, 2b), has a configured periodicity as well (e.g., 20 ms), and is a narrow bit pipe containing at most 11 bits.

Recent development in 3GPP has led to the discussion of two-dimensional antenna arrays, where each antenna element has an independent phase and amplitude control, thereby enabling beamforming both in the vertical and the horizontal dimensions. Such antenna arrays may be at least partially described by the number of antenna columns corresponding to the horizontal dimension $N_h$, the number of antenna rows corresponding to the vertical dimension $N_v$, and the number of dimensions corresponding to different polarizations $N_p$. Thus, the total number of antennas is $N=N_h N_v N_p$.

FIG. 7 illustrates an example of a two-dimensional antenna array of cross-polarized antenna elements. More particularly, FIG. 7 illustrates an example of an antenna with $N_h=4$ horizontal antenna elements and $N_v=8$ vertical antenna elements. It furthermore consists of cross-polarized antenna elements, meaning that the number of polarization states $N_p=2$. Such an antenna can be denoted as an 8×4 antenna array with cross-polarized antenna elements. The right hand side illustrates an example port layout, with 2 vertical ports and 4 horizontal ports, which could for instance be obtained by virtualizing each port by 4 vertical antenna elements. Hence, assuming cross-polarized ports are present, the UE will measure 16 antenna ports in this example.

From a wireless device perspective, however, the actual number of antenna array elements is not visible to the wireless device, but rather the antenna ports, where each port corresponds to a CSI reference signal. The wireless device can thus measure the channel from each of these ports. Therefore, we introduce a 2D port layout, described by the number of antenna ports corresponding to the horizontal dimension $M_h$, the number of antenna rows corresponding to the vertical dimension $M_v$, and the number of dimensions corresponding to different polarizations $M_p$. The total number of antenna ports is thus $M=M_h M_v M_p$. The mapping of these ports onto the N antenna elements is an eNB implementation issue, and thus not visible by the wireless device. The wireless device does not even know the value of N; it only knows the value of the number of ports M.

Precoding may be interpreted as multiplying the signal with different beamforming weights for each antenna port prior to transmission. A typical approach is to tailor the precoder to the antenna form factor (i.e., taking into account $M_h$, $M_v$ and $M_p$ when designing the precoder codebook).

A common approach when designing precoder codebooks tailored for 2D antenna arrays is to combine precoders tailored for a horizontal array and a vertical array of antenna ports, respectively, by means of a Kronecker product. This means that (at least part of) the precoder can be described as a function of:

$$W_H \otimes W_V$$

where $W_H$ is a horizontal precoder taken from a (sub)-codebook $X_H$ containing $N_H$ codewords. Similarly, $W_V$ is a vertical precoder taken from a (sub)-codebook $X_V$ containing $N_V$ codewords. The joint codebook, denoted by $X_H \otimes X_V$, thus contains $N_H \cdot N_V$ codewords. The codewords of $X_H$ are indexed with $k=0, \ldots, N_H-1$, the codewords of $X_V$ are indexed with $l=0, \ldots, N_V-1$, and the codewords of the joint codebook $X_H \otimes X_V$ are indexed with $m=N_V \cdot k+l$ (meaning that $m=0, \ldots, N_H \cdot N_V-1$).

For Release 12 wireless devices and earlier, only a codebook feedback for a 1D port layout is supported, with 2, 4 or 8 antenna ports. Hence, the codebook is designed assuming these ports are arranged on a straight line.

A method has been proposed to use measurements on fewer CSI-RS ports for periodic CSI reports than measurements for the aperiodic CSI reports. In one scenario, the periodic CSI report framework is identical to the legacy terminal periodic CSI report framework. Hence, periodic CSI reports with 2, 4 or 8 CSI-RS ports are used for the P-CSI reporting, and additional ports are used for the A-CSI reporting. From the UE and eNB perspective, the operations related to periodic CSI reporting is identical to legacy operation. The full, large 2D port layout CSI measurements of up to 64 ports or even more is only present in the aperiodic reports. Since A-CSI is carried over PUSCH, the payload can be much larger than the small 11-bit limit of the P-CSI using PUCCH format 2.

It has been agreed that for 12 or 16 ports, CSI-RS resources for class A (or non-precoded CSI-RS) CSI reporting is composed as an aggregation of K CSI-RS configurations each with N ports. In case of CDM-2, the K CSI-RS resource configurations indicate CSI-RS RE locations according to legacy resource configurations in TS 36.211. For 16 ports: (N,K)=(8,2) or (2,8). For 12 ports: (N,K)=(4,3), (2,6). The ports of the aggregated resource are as follows:

The aggregated port numbers are 15, 16, . . . 30 (for 16 CSI-RS ports)

The aggregated port numbers are 15, 16, . . . 26 (for 12 CSI-RS ports).

For a given P antenna ports, the Release 10 and 12 precoding codebooks are designed so that the P/2 first antenna ports (e.g., 15-22 for P=16) should map to a set of co-polarized antennas and the P/2 last antenna ports (e.g., 23-30 for P=16) are mapped to another set of co-polarized antennas, with an orthogonal polarization to the first set. For example, the first subset is associated with a first length-P/2 vector of a length-P precoding vector in a codebook. The second subset is associated with a second length-P/2 vector of the length-P precoding vector, wherein the second length-P/2 is obtained by scaling the first length-P/2 vector by a complex number. This is thus targeting cross-polarized antenna arrays, or more generally, antenna arrays with at last two distinct polarization states.

FIG. 8 illustrates the port numbering for P=8 antenna ports. The codebook principles for the rank 1 case are that a DFT "beam" vector is chosen for each set of P/2 ports and a phase shift with QPSK alphabet is used to co-phase the two sets of antenna ports. A rank 1 codebook is thus constructed as:

$$\begin{pmatrix} a \\ ae^{i\omega} \end{pmatrix}$$

where $a$ is a length P/2 vector that forms a beam for the first and second polarizations, respectively, and $\omega$ is a co-phasing scalar that co-phases the two orthogonal polarizations.

SUMMARY

According to certain embodiments, a method in a network node is disclosed. The method comprises selecting a subset from a predetermined set of P CSI-RS ports for receiving channel information. The network node comprises an antenna array with controllable polarization. Each CSI-RS port corresponds to a combination of a set of resource elements and an antenna port of said antenna array. The predetermined set comprises a first number $P_1$ of CSI-RS ports with a first polarization state and a second number $P_2$ of CSI-RS ports with a second polarization state. The first and second polarization states are distinct. The method further comprises populating the subset with Q CSI-RS ports in such manner that the ratio of CSI-RS ports respectively having the first and second polarization states is equal to the ratio of the first and second numbers.

According to certain embodiments, a method in a wireless device served by a network node of a wireless communication network is provided. The network node is equipped with P=8 or P>8 antenna ports for transmitting signals to the wireless device. The method includes receiving, from the network node, a CSI-RS setup that includes K CSI-RS configurations each with N CSI_RS ports and an antenna configuration of the network node with P antenna ports. A subset of Q antenna ports is determined from the P antenna ports. Channel information is measured based on the reference signals associated with the subset of antenna ports. The measure channel information is reported to the network node.

According to certain embodiments, a method in a wireless device of a wireless communication network is provided. The wireless device is served by a plurality of network nodes, and each network node includes an antenna array. The method includes receiving a reference signal in a specific set of resource elements from a first network node while being served by the first network node. Feedback information is transmitted to the first network node. The reference signal or the combination of the reference signal and the set of resource elements is indicative of an identifier. While being served by a second network node distinct from the first network node, a reference signal in said set of specific resource elements is received from the second network node. Feedback information is transmitted to the second network node, and the reference signal or the combination of the reference signal and the set of resource elements is indicative of an identifier. The reference signal is received with different beamforming from the first and second network nodes in spite of the equality of the identifiers.

According to certain embodiments, a network node is provided. The network node includes an antenna array with controllable polarization, and one or more processors. The one or more processors are configured to select a subset from a predetermined set of P CSI-RS ports for receiving channel information, wherein each CSI-RS port corresponds to a combination of a set of resource elements and an antenna port of said antenna array, the predetermined set comprises a first number $P_1$ of CSI-RS ports with a first polarization state and a second number $P_2$ of CSI-RS ports with a second polarization state, the first and second polarization states being distinct. The one or more processors are further configured to populate the subset with Q CSI-RS ports in such manner that the ratio of CSI-RS ports respectively having the first and second polarization states is equal to the ratio of the first and second numbers.

According to certain embodiments, a wireless device configured to be served by a network node in a wireless communication network is provided. The network node is equipped with P=8 or P>8 antenna ports for transmitting signals to the wireless device. The wireless device includes one or more processors. The one or more processors are configured to receive, from the network node, a CSI-RS set up comprising K CSI reference signal configurations each with N CSI-RS ports and an antenna configuration of the network node with P antenna ports. The one or more processors are further configured to determine a subset of Q antenna ports from the P antenna ports and measure channel information based on the reference signals associated with the subset of antenna ports. The measured channel information is reported to the network node.

According to certain embodiments, a wireless device configured to be served by a plurality of network nodes each comprising an antenna array is provided. The wireless device includes one or more processors. The one or more processors are configured to, while being served by a first network node, receive a reference signal in a specific set of resource elements from the first network node and transmit feedback information to the first network node. The reference signal or the combination of the reference signal and the set of resource elements is indicative of an identifier. The one or more processors are further configured to, while being served by a second network node distinct from the first network node, receive a reference signal in said specific resource element from the second network node and transmit feedback information to the second network node. The reference signal or the combination of the reference signal and the set of resource elements is indicative of an identifier, and the wireless device is configured to receive the reference signal with different beamforming from the first and second network nodes in spite of equality of the identifiers.

According to certain embodiments, a computer program product comprising instructions stored on non-transient computer-readable media which, when executed by a processor, performs the acts of: selecting a subset from a predetermined set of P CSI-RS ports for receiving channel information, wherein each CSI-RS port corresponds to a combination of a set of resource elements and an antenna port of an antenna array, the predetermined set comprises a first number $P_1$ of CSI-RS ports with a first polarization state and a second number $P_2$ of CSI-RS ports with a second polarization state, the first and second polarization states being distinct; and populating the subset with Q CSI-RS ports in such manner that the ratio of CSI-RS ports respectively having the first and second polarization states is equal to the ratio of the first and second numbers.

According to certain embodiments, a computer program product comprising instructions stored on non-transient computer-readable media which, when executed by a processor, performs the acts of: while being served by a first network node, receiving a reference signal in a set of specific resource elements from the first network node and transmitting feedback information to the first network node, wherein the reference signal or the combination of the reference signal and the set of resource elements is indicative of an identifier; and while being served by a second network node distinct from the first network node, receiving a reference signal in said set of specific resource elements from the second network node and transmitting feedback information to the second network node, wherein the reference signal or the combination of the reference signal and the set of resource elements is indicative of an identifier. The reference signal is received with different beamforming from the first and second network nodes in spite of equality of the identifiers.

According to certain embodiments, a computer program product comprising instructions stored on non-transient computer-readable media which, when executed by a processor, performs the acts of: receiving, from a network node, a CSI-RS setup comprising K CSI reference signal configurations each with N CSI-RS ports and an antenna configuration of the network node with P antenna ports, wherein the network node is equipped with P=8 or P>8 antenna ports for transmitting signals to the wireless device; determining a subset of Q antenna ports from the P antenna ports; measuring channel information based on the reference signals associated the subset of antenna ports; and reporting the measured channel information to the network node. In particular, each CSI reference signal configuration may have N CSI-RS ports and an antenna configuration of a serving cell of the network node.

Certain embodiments of the present disclosure may provide one or more technical advantages. As one example, certain embodiments may advantageously not require additional signaling for configuring CSI-RS ports for periodic CSI reporting. As another example, legacy terminals can be supported with the same eNB antenna array as FD-MIMO supporting terminals without additional CSI-RS overhead, since the ports used for a first type of feedback is a subset of the ports used for a second type of feedback. As yet another example, the codebooks, which are designed for cross polarized antenna arrays where the first half of antenna ports are on one polarization and the second half of antenna ports are on a different polarization, can be used both for the first type and the second type of feedback.

Other advantages may be readily apparent to one having skill in the art. Certain embodiments may have none, some, or all of the recited advantages.

BRIEF DESCRIPTION OF THE DRAWINGS

For a more complete understanding of the disclosed embodiments and their features and advantages, reference is now made to the following description, taken in conjunction with the accompanying drawings, in which:

FIG. 7 illustrates an example of a two-dimensional antenna array of cross-polarized antenna elements;

DETAILED DESCRIPTION

Figure 1:
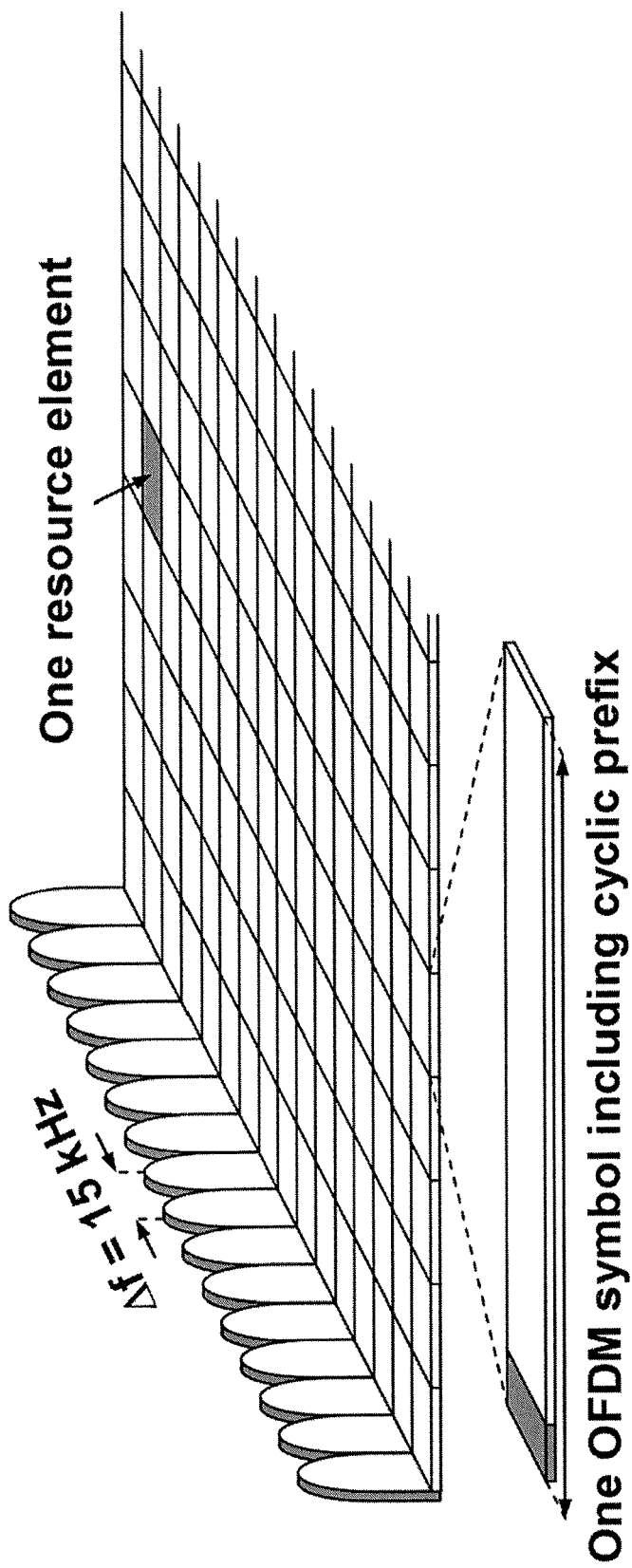
FIG. 1 illustrates the basic LTE downlink physical resource.
Figure 2:
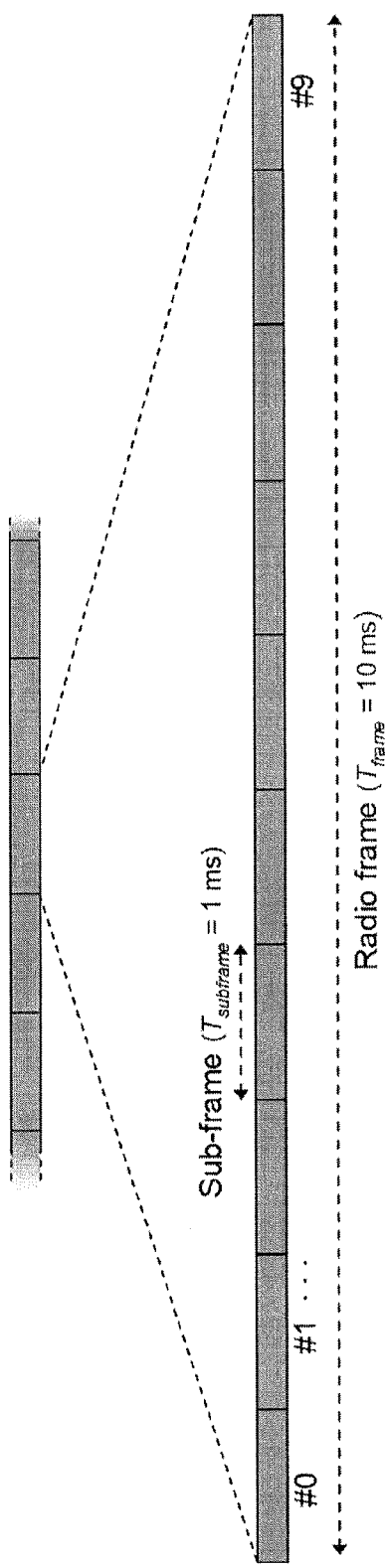
FIG. 2 illustrates the LTE time-domain structure.
Figure 3:
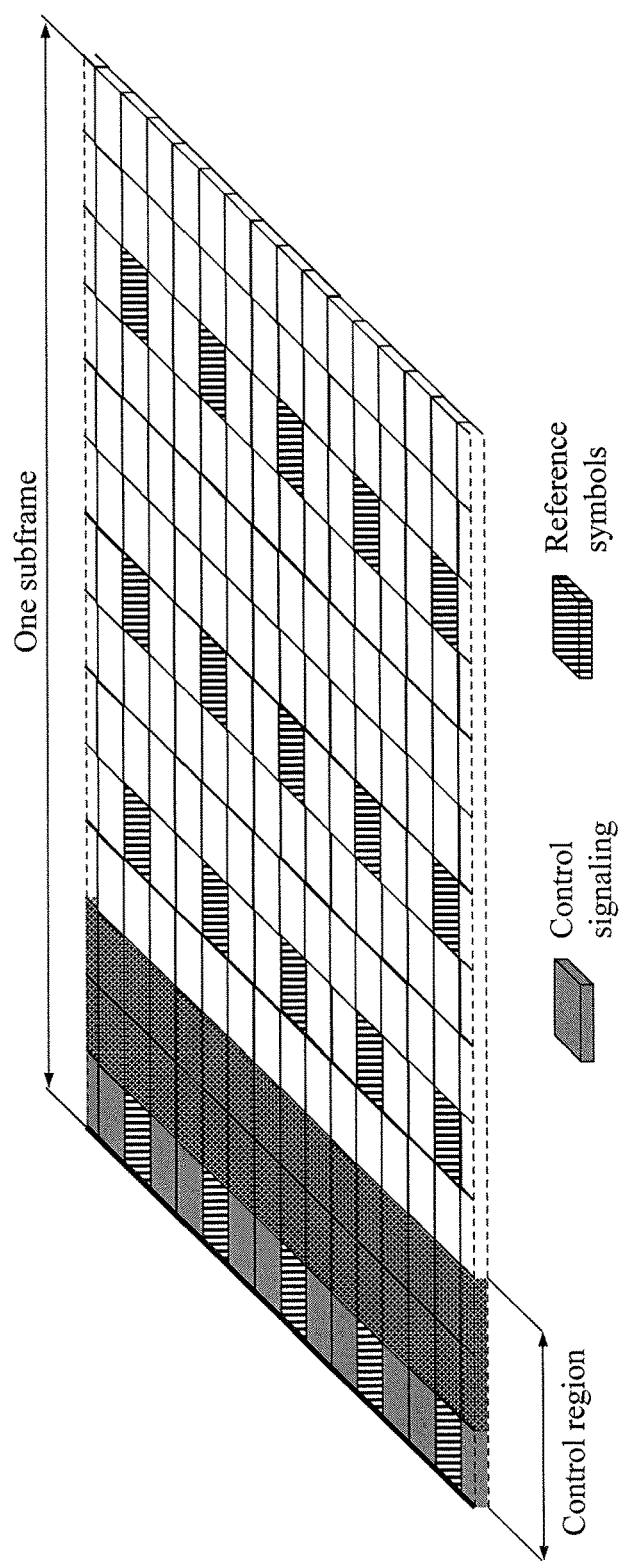
FIG. 3 illustrates an example downlink subframe.
Figure 4:
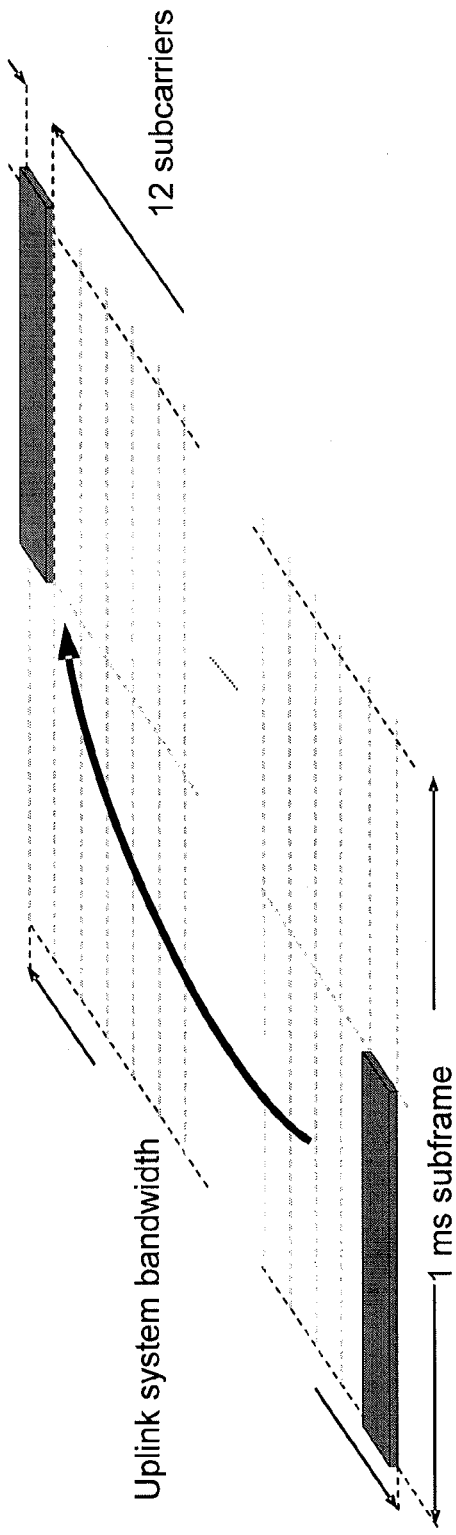
FIG. 4 illustrates uplink L1/L2 control signaling transmission on PUCCH.
Figure 5:
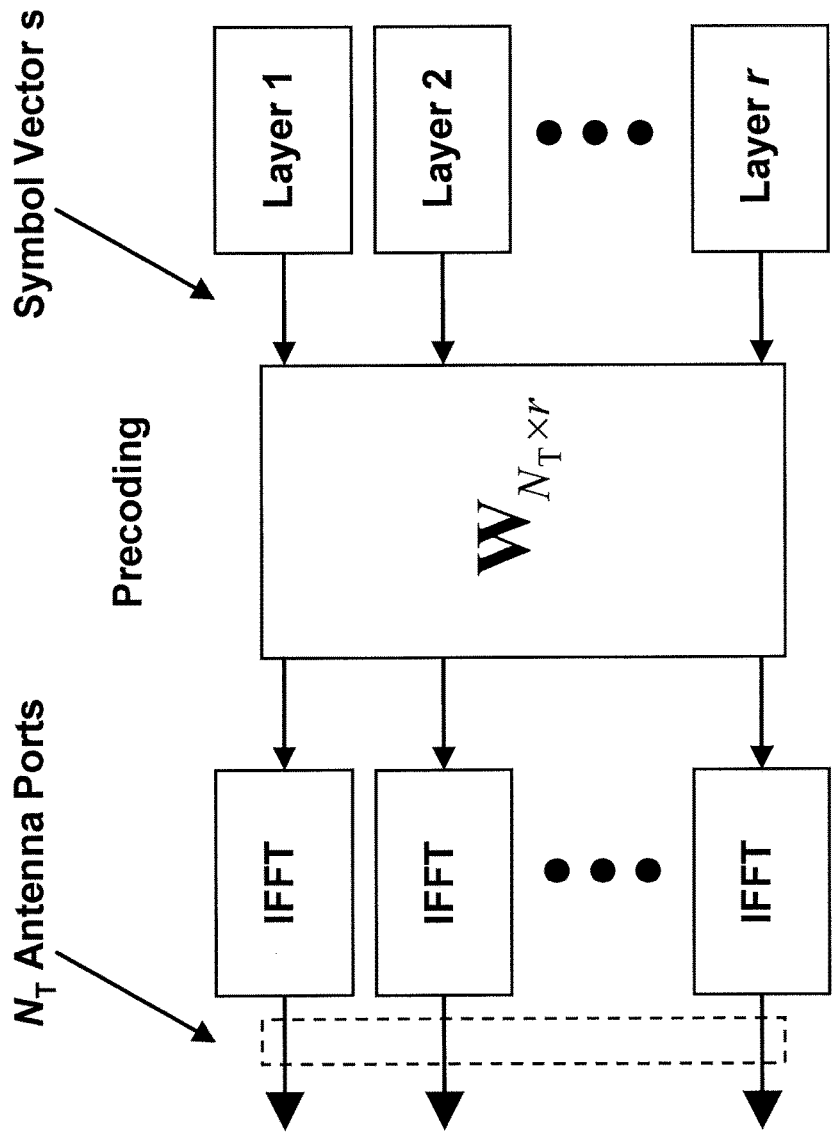
FIG. 5 illustrates an example of spatial multiplexing operation.

In 3GPP Release 13, additional antenna ports are specified for CSI feedback, and up to 16 ports can be supported. In future releases, even more ports may be supported (e.g., 32). However, legacy (Release 12 or earlier) wireless devices support at most 8 ports CSI measurements. Accordingly, there is a need to support legacy terminals with network nodes having more than 8 CSI-RS ports in an efficient manner that does not increase CSI-RS overhead. More specifically, a problem is how to select a subset of the Release 13 CSI-RS ports for legacy wireless devices and still match to the legacy codebook design for cross-polarized antenna arrays. Even for Release 13 wireless devices, it is beneficial if fewer CSI-RS ports are used for periodic reporting, and the full set of CSI-RS antenna ports is used for aperiodic reporting. A problem then exists with respect to how to select a subset of the configured full set of CSI-RS ports for CSI measurement and reporting.

The present disclosure contemplates various embodiments that may address these and other deficiencies. In the following description, we denote the use of P>8 ports as the second type of CSI reporting (or feedback) and the use of Q≤8 ports as the first type of CSI reporting (or feedback). The first type can thus be used for legacy terminal CSI reporting which do not support greater than 8 ports, or it can be used for PUCCH reporting for wireless devices of second type, e.g. Release 13, (even if they support greater than 8 ports).

In certain embodiments, a first type of feedback and a second type of feedback may be defined where the first type uses Q≤8 ports and the second type is P>8 ports. The second type of feedback is arranged so that first P/2 ports are of one polarization, while the second half of P/2 ports are of a different (orthogonal) polarization. Additionally, the CSI-RS resources used for the P ports are an aggregation of multiple CSI-RS configurations, each having N (N<P) ports.

The Q CSI-RS ports used for a first type of feedback is then chosen such that (either or both):
1. They have the same property (as described above) that the P>Q CSI-RS ports used for the second type of feedback (i.e., the first Q/2 ports are with one polarization while the second half of Q/2 ports are with a different (orthogonal) polarization).
2. They occupy a subset or one of the aggregated CSI-RS configurations used for defining or configuring ports of the second type of feedback.

In certain embodiments, a method for configuring a first set and a second set of CSI-RS resources and the corresponding CSI-RS antenna ports in a network is disclosed.

The first set may have Q ports, and the second set may have P>Q ports. The second set may contain an aggregation of K CSI-RS configurations, each having N ports, such that P=NK. The P/2 first ports are mapped to antennas of a first polarization, and the P/2 last ports are mapped to antennas of a second polarization. A mapping of the P ports in the second set of resources to the N ports in each of the K CSI-RS configurations is established. Then, a mapping of ports in the first set of resources to ports in the second set of resources is established so that the Q/2 first ports are mapped to antennas of a first polarization, and the Q/2 last ports are mapped to antennas of a second polarization.

In some cases, the Q ports are mapped to the N ports of one of the K configurations used for aggregating the second set of resources. The ports of the second set of resources may be numbered so that the P/2 first ports are mapped to antennas of a first polarization, and the P/2 last ports are mapped to antennas of a second polarization.

The various embodiments described herein may advantageously not require additional signaling for configuring CSI-RS ports for periodic CSI reporting. In addition, legacy terminals can be supported with the same eNB antenna array as FD-MIMO supporting terminals without additional CSI-RS overhead, since the ports used for first type of CSI feedback is a subset of the ports used for second type of CSI feedback. Furthermore, the codebooks, which are designed for cross polarized antenna arrays where the first half of antenna ports are of one polarization and the second half of antenna ports are of a different polarization, can be used both for the first type and the second type of feedback.

Figure 9:
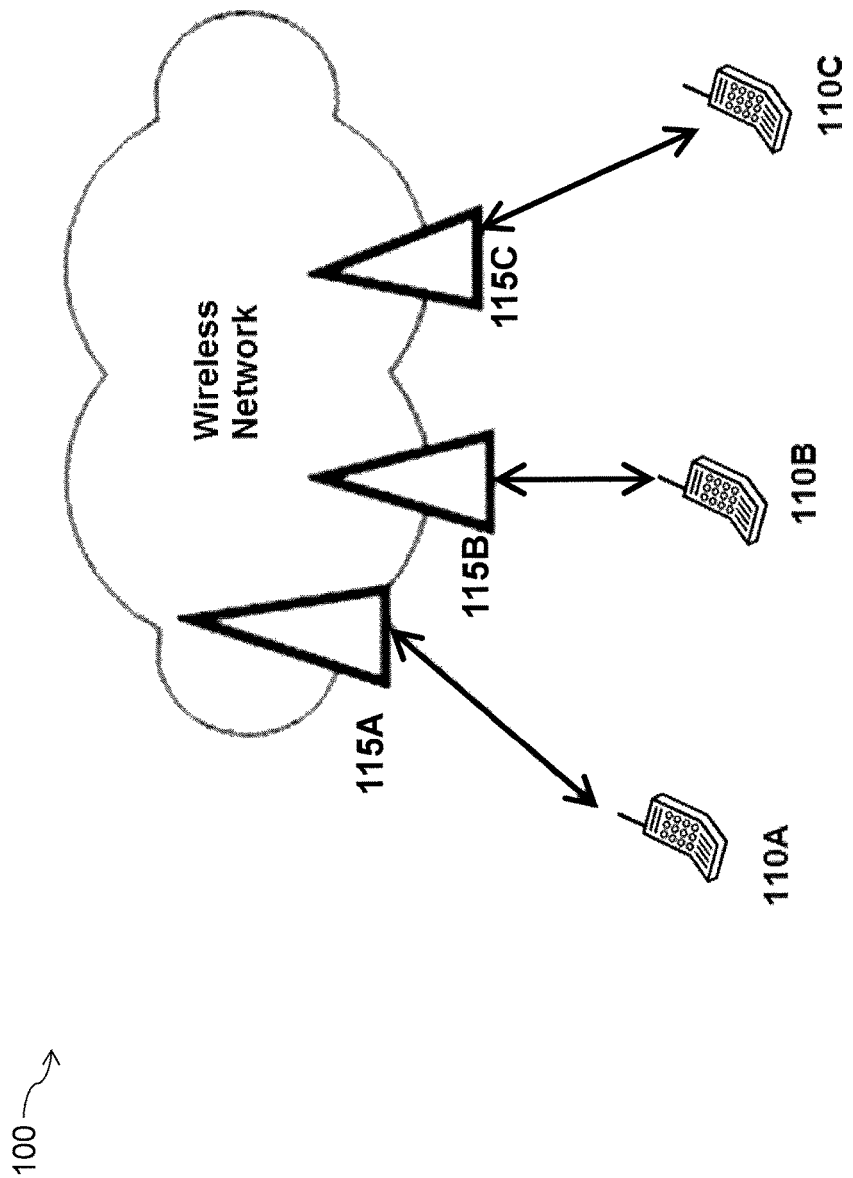
FIG. 9 is a block diagram illustrating an embodiment of a network, in accordance with certain embodiments.

FIG. 9 is a block diagram illustrating an embodiment of a network 100, in accordance with certain embodiments. Network 100 includes one or more wireless devices 110A-C, which may be interchangeably referred to as wireless devices 110 or UEs 110, and network nodes 115A-C, which may be interchangeably referred to as network nodes 115 or eNodeBs 115. Wireless devices 110 may communicate with network nodes 115 over a wireless interface. For example, wireless device 110A may transmit wireless signals to one or more of network nodes 115, and/or receive wireless signals from one or more of network nodes 115. The wireless signals may contain voice traffic, data traffic, control signals, and/or any other suitable information. In some embodiments, an area of wireless signal coverage associated with a network node 115 may be referred to as a cell. In some embodiments, wireless devices 110 may have D2D capabilities. Thus, wireless devices 110 may be able to receive signals from and/or transmit signals directly to another wireless device. For example, wireless device 110A may be able to receive signals from and/or transmit signals to wireless device 110B.

In certain embodiments, network nodes 115 may interface with a radio network controller. The radio network controller may control network nodes 115 and may provide certain radio resource management functions, mobility management functions, and/or other suitable functions. In certain embodiments, the functions of the radio network controller may be included in network node 115. The radio network controller may interface with a core network node. In certain embodiments, the radio network controller may interface with the core network node via an interconnecting network. The interconnecting network may refer to any interconnecting system capable of transmitting audio, video, signals, data, messages, or any combination of the preceding. The interconnecting network may include all or a portion of a public switched telephone network (PSTN), a public or private data network, a local area network (LAN), a metropolitan area network (MAN), a wide area network (WAN), a local, regional, or global communication or computer network such as the Internet, a wireline or wireless network, an enterprise intranet, or any other suitable communication link, including combinations thereof.

In some embodiments, the core network node may manage the establishment of communication sessions and various other functionalities for wireless devices 110. Wireless devices 110 may exchange certain signals with the core network node using the non-access stratum layer. In non-access stratum signaling, signals between wireless devices 110 and the core network node may be transparently passed through the radio access network. In certain embodiments, network nodes 115 may interface with one or more network nodes over an internode interface. For example, network nodes 115A and 115B may interface over an X2 interface.

As described above, example embodiments of network 100 may include one or more wireless devices 110, and one or more different types of network nodes capable of communicating (directly or indirectly) with wireless devices 110. Wireless device 110 may refer to any type of wireless device communicating with a node and/or with another wireless device in a cellular or mobile communication system. Examples of wireless device 110 include a mobile phone, a smart phone, a PDA (Personal Digital Assistant), a portable computer (e.g., laptop, tablet), a sensor, a modem, a machine-type-communication (MTC) device/machine-to-machine (M2M) device, laptop embedded equipment (LEE), laptop mounted equipment (LME), USB dongles, a D2D capable device, or another device that can provide wireless communication. A wireless device 110 may also be referred to as UE, a station (STA), a device, or a terminal in some embodiments. Also, in some embodiments, generic terminology, "radio network node" (or simply "network node") is used. It can be any kind of network node, which may comprise a Node B, base station (BS), multi-standard radio (MSR) radio node such as MSR BS, eNode B, network controller, radio network controller (RNC), base station controller (BSC), relay donor node controlling relay, base transceiver station (BTS), access point (AP), transmission points, transmission nodes, RRU, RRH, nodes in distributed antenna system (DAS), core network node (e.g. MSC, MME etc.), O&M, OSS, SON, positioning node (e.g. E-SMLC), MDT, or any suitable network node. Example embodiments of wireless devices 110, network nodes 115, and other network nodes (such as radio network controller or core network node) are described in more detail with reference to FIGS. 10, 18, and 22, respectively.

Although FIG. 9 illustrates a particular arrangement of network 100, the present disclosure contemplates that the various embodiments described herein may be applied to a variety of networks having any suitable configuration. For example, network 100 may include any suitable number of wireless devices 110 and network nodes 115, as well as any additional elements suitable to support communication between wireless devices or between a wireless device and another communication device (such as a landline telephone). Furthermore, although certain embodiments may be described as implemented in a long term evolution (LTE) network, the embodiments may be implemented in any appropriate type of telecommunication system supporting any suitable communication standards and using any suitable components, and are applicable to any radio access technology (RAT) or multi-RAT systems in which the wireless device receives and/or transmits signals (e.g., data). For example, the various embodiments described herein may be applicable to LTE, LTE-Advanced, UMTS, HSPA, GSM, cdma2000, WiMax, WiFi, another suitable radio access technology, or any suitable combination of one or more radio access technologies. Although certain embodiments may be described in the context of wireless transmissions in the downlink, the present disclosure contemplates that the various embodiments are equally applicable in the uplink.

Figure 10:
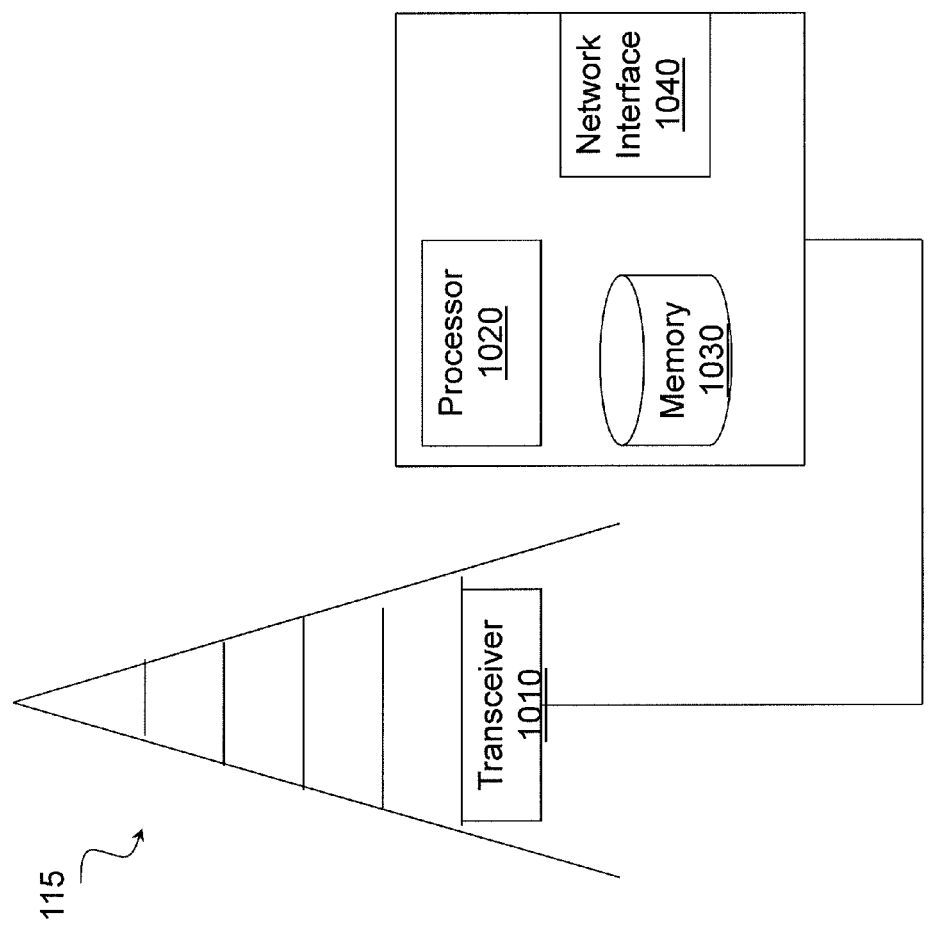
FIG. 10 is a block schematic of an exemplary network node, in accordance with certain embodiments.

FIG. 10 is a block schematic of an exemplary network node 115, in accordance with certain embodiments. As described above, network node 115 may be any type of radio network node or any network node that communicates with a wireless device and/or with another network node. Examples of a network node 115 are provided above.

Network nodes 115 may be deployed throughout network 100 as a homogenous deployment, heterogeneous deployment, or mixed deployment. A homogeneous deployment may generally describe a deployment made up of the same (or similar) type of network nodes 115 and/or similar coverage and cell sizes and inter-site distances. A heterogeneous deployment may generally describe deployments using a variety of types of network nodes 115 having different cell sizes, transmit powers, capacities, and inter-site distances. For example, a heterogeneous deployment may include a plurality of low-power nodes placed throughout a macro-cell layout. Mixed deployments may include a mix of homogenous portions and heterogeneous portions.

Network node 115 may include one or more of transceiver 1010, processor 1020, memory 1030, and network interface 1040. In some embodiments, transceiver 1010 facilitates transmitting wireless signals to and receiving wireless signals from wireless device 110 (e.g., via an antenna), processor 1020 executes instructions to provide some or all of the functionality described above as being provided by a network node 115, memory 1030 stores the instructions executed by processor 1020, and network interface 1040 communicates signals to backend network components, such as a gateway, switch, router, Internet, Public Switched Telephone Network (PSTN), core network nodes or radio network controllers 130, etc.

In certain embodiments, network node 115 may be capable of using multi-antenna techniques, and may be equipped with multiple antennas and capable of supporting MIMO techniques. The one or more antennas may have controllable polarization. In other words, each element may have two co-located sub elements with different polarizations (e.g., 90 degree separation as in cross-polarization), so that different sets of beamforming weights will give the emitted wave different polarization.

Processor 1020 may include any suitable combination of hardware and software implemented in one or more modules to execute instructions and manipulate data to perform some or all of the described functions of network node 115. In some embodiments, processor 1020 may include, for example, one or more computers, one or more central processing units (CPUs), one or more microprocessors, one or more applications, and/or other logic.

Memory 1030 is generally operable to store instructions, such as a computer program, software, an application including one or more of logic, rules, algorithms, code, tables, etc. and/or other instructions capable of being executed by a processor. Examples of memory 1030 include computer memory (for example, Random Access Memory (RAM) or Read Only Memory (ROM)), mass storage media (for example, a hard disk), removable storage media (for example, a Compact Disk (CD) or a Digital Video Disk (DVD)), and/or or any other volatile or non-volatile, non-transitory computer-readable and/or computer-executable memory devices that store information.

In some embodiments, network interface 1040 is communicatively coupled to processor 1020 and may refer to any suitable device operable to receive input for network node 115, send output from network node 115, perform suitable processing of the input or output or both, communicate to other devices, or any combination of the preceding. Network interface 1040 may include appropriate hardware (e.g., port, modem, network interface card, etc.) and software, including protocol conversion and data processing capabilities, to communicate through a network.

Other embodiments of network node 115 may include additional components beyond those shown in FIG. 10 that may be responsible for providing certain aspects of the radio network node's functionality, including any of the functionality described above and/or any additional functionality (including any functionality necessary to support the solutions described above). The various different types of network nodes may include components having the same physical hardware but configured (e.g., via programming) to support different radio access technologies, or may represent partly or entirely different physical components.

In certain embodiments, network node 115 signals to a wireless device 110 the port layout $M_1 \times M_2$, where $M_i (i=1,2)$ is the number of antenna ports per polarization for dimension i, and a configuration of CSI-RS reference signals corresponding to a total of $P=2M_1M_2$) CSI-RS ports consisting of an aggregation of K N-port CSI-RS configurations as follows:

CSI-RS configuration with k=0: N CSI-RS ports

CSI-RS configuration with k=1: N CSI-RS ports ... ...

CSI-RS configuration with k=K−1: CSI-RS ports, where $P=K*N$ and $N \in \{2,4,8\}$. Hence, network node 115 signals a list of these K CSI-RS configurations by RRC to wireless device 110.

Figure 11:
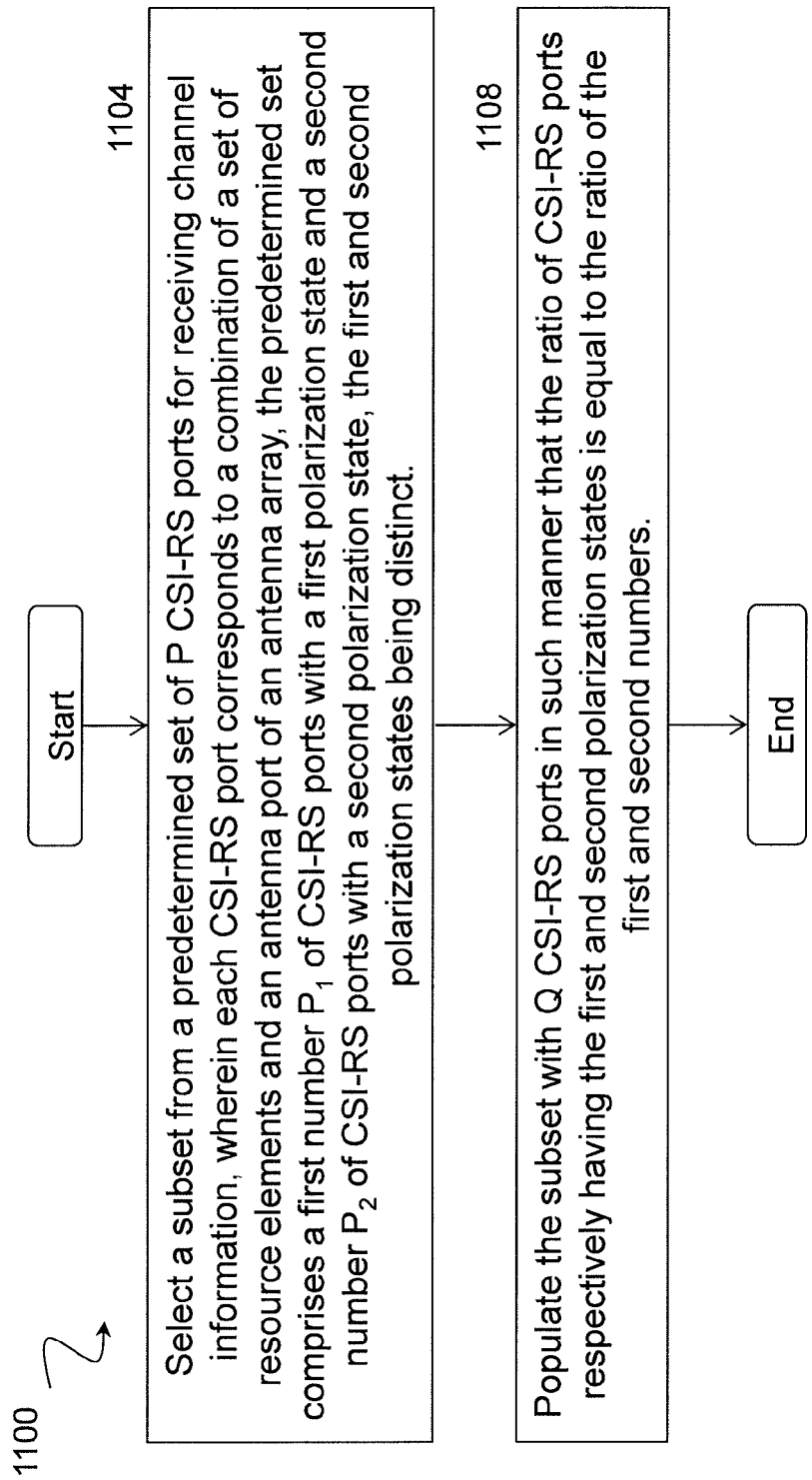
FIG. 11 is a flow diagram of a method in a network node, in accordance with certain embodiments.

FIG. 11 illustrates a flow diagram of a method 1100 in a network node 115, in accordance with certain embodiments. The method begins at step 1104 with the selection, by network node 115, of a subset from a predetermined set of P CSI-RS ports for receiving channel information. Each CSI-RS port may correspond to a combination of a set of resource elements and an antenna port of an antenna array. The predetermined set comprises a first number $P_1$ of CSI-RS ports with a first polarization state and a second number $P_2$ of CSI-RS ports with a second polarization state, where the first and second polarization states are distinct.

At step 1108, the subset is populated with Q CSI-RS ports in such manner that the ratio of CSI-RS ports respectively having the first and second polarization states is equal to the ratio of the first and second numbers. In certain embodiments, the subset may be populated with $QP_1/(P_1+P_2)$ CSI-RS ports having the first polarization state and $QP_2/(P_1+P_2)$ CSI-RS ports having the second polarization state. In certain embodiments, $P_1$ and $P_2$ may be equal. In certain embodiments, half of the CSI-RS ports in the subset may have the first polarization state and half of the CSI-RS ports in the subset have the second polarization state.

In a first particular embodiment, for example, the CSI measurement of first type of report may be performed over the CSI-RS ports from multiple, or all, of the aggregated CSI-RS configurations used in the second type of report. When numbering the antenna ports for the second type of reporting, having P>8 CSI-RS ports, then the following expression may be used:

$$p = \begin{cases} r + \dfrac{N}{2}k & r = 15, 16, \ldots, 14 + \dfrac{N}{2} \\ r + \dfrac{N}{2}(k + K - 1) & r = 15 + \dfrac{N}{2}, \ldots, 14 + N \end{cases}$$

where k (=0, . . . , K−1) correspond to the k-th component of the K CSI-RS configurations (each having N antenna ports) and r is the port index of each component CSI-RS configuration. Each-CSI-RS port in the predetermined set may be associated with an identifier selected from an ordered set. The first number P1 of CSI-RS ports may be associated with identifiers in a first predetermined range and a second number P2 of CSI-RS ports may be associated with identifiers in a second predetermined range. The subset may be populated with a number of CSI-RS ports from a lower portion of the first predetermined range and an equal number of CSI-Reports from a lower portion of the second predetermined range, in a particular embodiment. However, it is may be recognized that the subset may also be populated with a number of ports from an upper portion of each predetermined range, a mid portion of each predetermined range, a lower portion of each predetermined range, or any combination thereof of the predetermined ranges. Such port numbering can also be summarized in Table 1 below for (N,K)=(8,2), (4,3) and Table 2 below for (N,K)=(2,8), (2,6).

Figure 12:
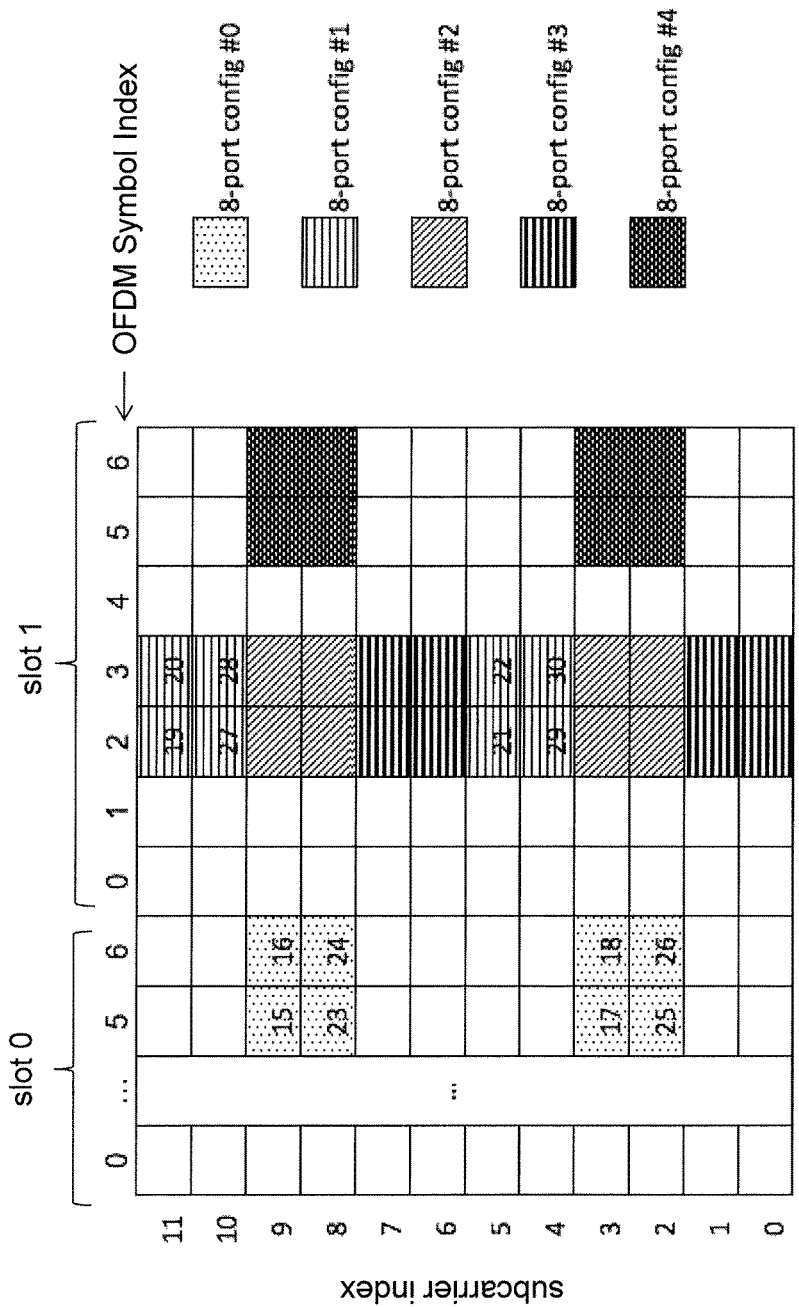
FIG. 12 shows an example of 16 ports CSI-RS port indexing with aggregation of two 8-port CSI-RS configurations, in accordance with certain embodiments.

{15,16,17,18,23,24,25,26} and the ports for the k=1 configuration are numbered as {19,20,21,22,27,28,29,30} as shown in FIG. 12. Now, the ports 15-22 are mapped to antennas of the first polarization and 23-30 to antennas of the second polarization. Hence, in this embodiment, each of the K CSI-RS configurations are mapped to cross-polarized antennas wherein the first half of ports (i.e., ports 15 to 22) are mapped to one polarization and the second half (i.e., ports 23 to 30) to the alternate polarization. The CSI-RS signals on adjacent OFDM symbols are actually code division multiplexed with a length 2 Orthogonal Cover Code (OCC). For simplicity of illustration, only a single port number is labelled in each RE in FIG. 12. For example, the CSI-RS signals of ports 15 and 16 are transmitted on both OFDM symbols 5 and 6 in slot 0. In addition, only the first resource block (RB) is shown, the same mapping also applies to other RBs in the whole system bandwidth of a network node.

Figure 13:
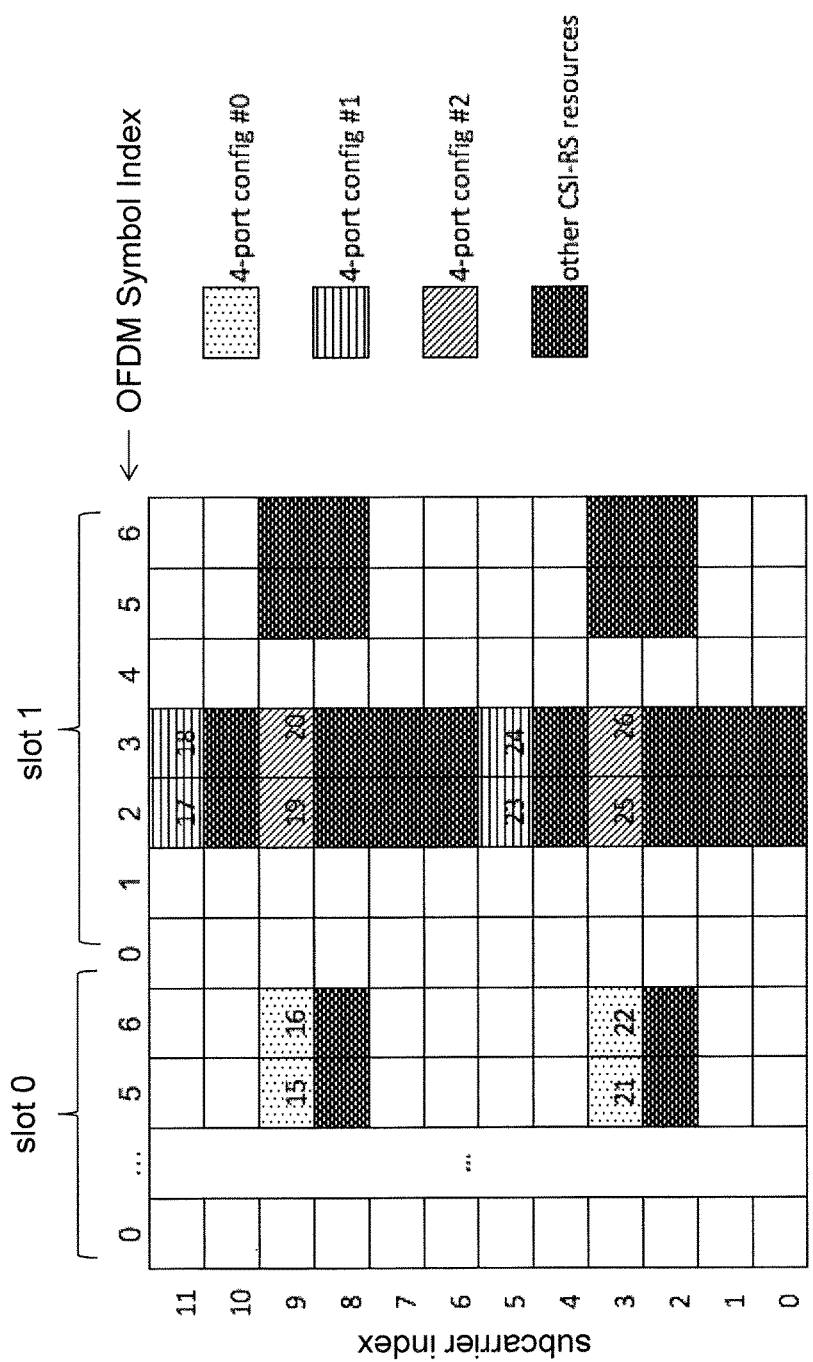
FIG. 13 illustrates another example having 12 ports CSI-RS port indexing with aggregation of three 4-antenna-port CSI-RS configurations, in accordance with certain embodiments.

FIG. 13 illustrates another example having 12 ports CSI-RS port indexing with aggregation of three 4-antenna-port CSI-RS configurations: configurations #0 (k=0), #1 (k=1) and #2 (k=2). The example illustrated in FIG. 13 includes 12 CSI-RS ports configured with aggregation with three 4-antenna-port CSI-RS configurations (i.e., N=4, K=3). Again, each of the K CSI-RS configurations are mapped to cross-polarized antennas wherein the first half of

TABLE 1

Mapping of 12 and 16 CSI-RS ports using aggregation of multiple eight (N = 8) and four (N = 4) ports CSI-RS configurations

| Port number (p) | | | | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|
| Port number of each component CSI-RS configuration (r) | K = 2, N = 8 | Aggregated configuration (k) | 0 | 15 | 16 | 17 | 18 | — | — | — | — | 19 | 20 | 21 | 22 | — | — | — | — |
| | | | 1 | — | — | — | — | 15 | 16 | 17 | 18 | — | — | — | — | 19 | 20 | 21 | 22 |
| | K = 3, N = 4 | Aggregated configuration (k) | 0 | 15 | 16 | — | — | — | — | — | — | 17 | 18 | — | — | — | — | — | — |
| | | | 1 | — | — | 15 | 16 | — | — | — | — | — | — | 17 | 18 | — | — | — | — |
| | | | 2 | — | — | — | — | 15 | 16 | — | — | — | — | — | — | 17 | 18 | — | — |

TABLE 2

Mapping of 12 and 16 CSI-RS ports using aggregation of eight (K = 8) and six (K = 6) 2-port (N = 2) CSI-RS configurations

| | | Aggregated CSI-RS Configuration (k) | | | | | | | | | | | | | | | |
|---|---|---|---|---|---|---|---|---|---|---|---|---|---|---|---|---|---|
| | | 0 | | 1 | | 2 | | 3 | | 4 | | 5 | | 6 | | 7 | |
| Port number of each component CSI-RS configuration (r) | | 15 | 16 | 15 | 16 | 15 | 16 | 15 | 16 | 15 | 16 | 15 | 16 | 15 | 16 | 15 | 16 |
| CSI-RS Port number (p) | K = 8, N = 2 | 15 | 23 | 16 | 24 | 17 | 25 | 18 | 26 | 19 | 27 | 20 | 28 | 21 | 29 | 22 | 30 |
| | K = 6, N = 2 | 15 | 21 | 16 | 22 | 17 | 23 | 18 | 24 | 19 | 25 | 20 | 26 | — | — | — | — |

In a particular embodiment, each CSI-RS port in the predetermined set may be associated with an identifier selected from an ordered set. The first number P1 of CSI-RS ports may be associated with identifiers in a first predetermined range and a second number P2 of CSI-RS ports may be associated with identifiers in a second predetermined range.

FIG. 12 shows an example of 16 ports CSI-RS port indexing with aggregation of two 8-port CSI-RS configurations (i.e., N=8, K=2): configuration #0 (k=0) and configuration #1 (k=1). For example, if N=8, K=2, P=16, then the CSI-RS ports for the k=0 configuration are numbered as ports (i.e., ports 15 to 20) are mapped to one polarization and the second half (i.e., ports 21 to 26) to the alternate polarization.

Since legacy wireless devices, or PUCCH for Release 13 wireless devices (i.e., first type of feedback), need to map to Q ports where Q/2 first ports are co-polarized, and last Q/2 ports also are co-polarized (but with orthogonal polarization) among the P>Q ports used for second type of feedback, the first type of feedback using Q antenna ports can select the first configuration (i.e., k=0) (or the second configuration) in the example shown in FIG. 12 for Q=8 and FIG. 13 for Q=4 and then the goal is directly achieved.

In certain embodiments, some generalized port numbering rules may be employed to achieve this objective for more general values of {M1,M2,P,Q,N,K} than what was assumed in the example described above. For example, the number of CSI-RS ports, $Q \in \{2,4,8\}$, used for legacy wireless devices 110 (that only support at most 8 ports) and for Release 13 wireless devices 110 using periodic CSI measurement and report on PUCCH may be determined by the following rule: $Q=\min(4\lfloor\max(M_1, M_2)/2\rfloor,8)$. The Q CSI-RS ports for first type of reporting can then be selected from the ports defined for the second type of reporting as follows:

$$\left\{15, 16, \ldots, 14+\frac{Q}{2}, 15+\frac{P}{2}, \ldots, 14+\frac{P}{2}+\frac{Q}{2}\right\}$$

Some examples of Q CSI-RS port numbering for first type of reporting are shown in Table 3 below.

TABLE 3

Examples of CSI-RS ports used for P-CSI measurement and report: linking Q to the size of 2D antenna array

| M₁ | M₂ | P | Q | Subset of CSI-RS ports for first type of reporting among ports used for second type of reporting | Port numbering for first type of reporting |
|---|---|---|---|---|---|
| 8 | 1 | 16 | 8 | 15, 16, 17, 18, 23, 24, 25, 26 | 15, 16, 17, 18, 19, 20, 21, 22 |
| 6 | 1 | 12 | 8 | 15, 16, 17, 18, 21, 22, 23, 24 | 15, 16, 17, 18, 19, 20, 21, 22 |
| 4 | 2 | 16 | 8 | 15, 16, 17, 18, 23, 24, 25, 26 | 15, 16, 17, 18, 19, 20, 21, 22 |
| 2 | 4 | 16 | 8 | 15, 16, 17, 18, 23, 24, 25, 26 | 15, 16, 17, 18, 19, 20, 21, 22 |
| 3 | 2 | 12 | 4 | 15, 16, 21, 22 | 15, 16, 17, 18 |
| 2 | 3 | 12 | 4 | 15, 16, 21, 22 | 15, 16, 17, 18 |

For instance, if M1=2 and M2=3, and Q=4 ports are used for the first type of CSI reporting and P=12 ports are used for second type of reporting, then ports 15-20 in the second type of reporting will use co-polarized antennas with one polarization, while ports 21-26 will also be a set of co-polarized antennas, but with orthogonal polarization with respect to ports 15-20. For the first type of reporting, the four ports 15-16 and 21-22 are selected among the ports used for second type of reporting. These ports are then re-numbered for the first type of reporting as ports 15-18 respectively to achieve the desired goal that the first Q/2 ports are co-polarized and the last Q/2 ports are also co-polarized but with alternative polarization.

Figure 14:
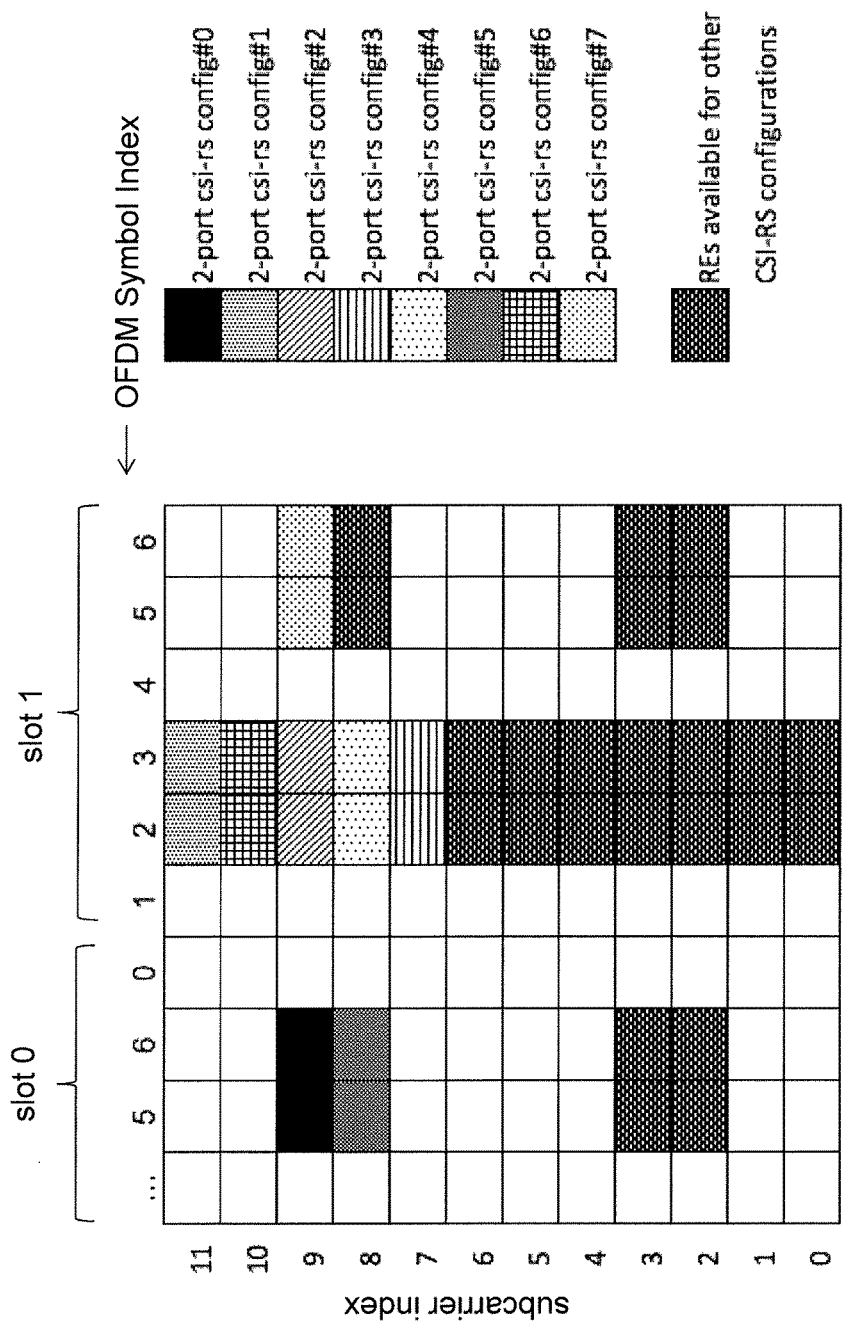
FIG. 14 illustrates an example of a 16-port CSI-RS configuration with aggregation of 8 legacy two ports CSI-RS configurations, in accordance with certain embodiments.
Figure 15:
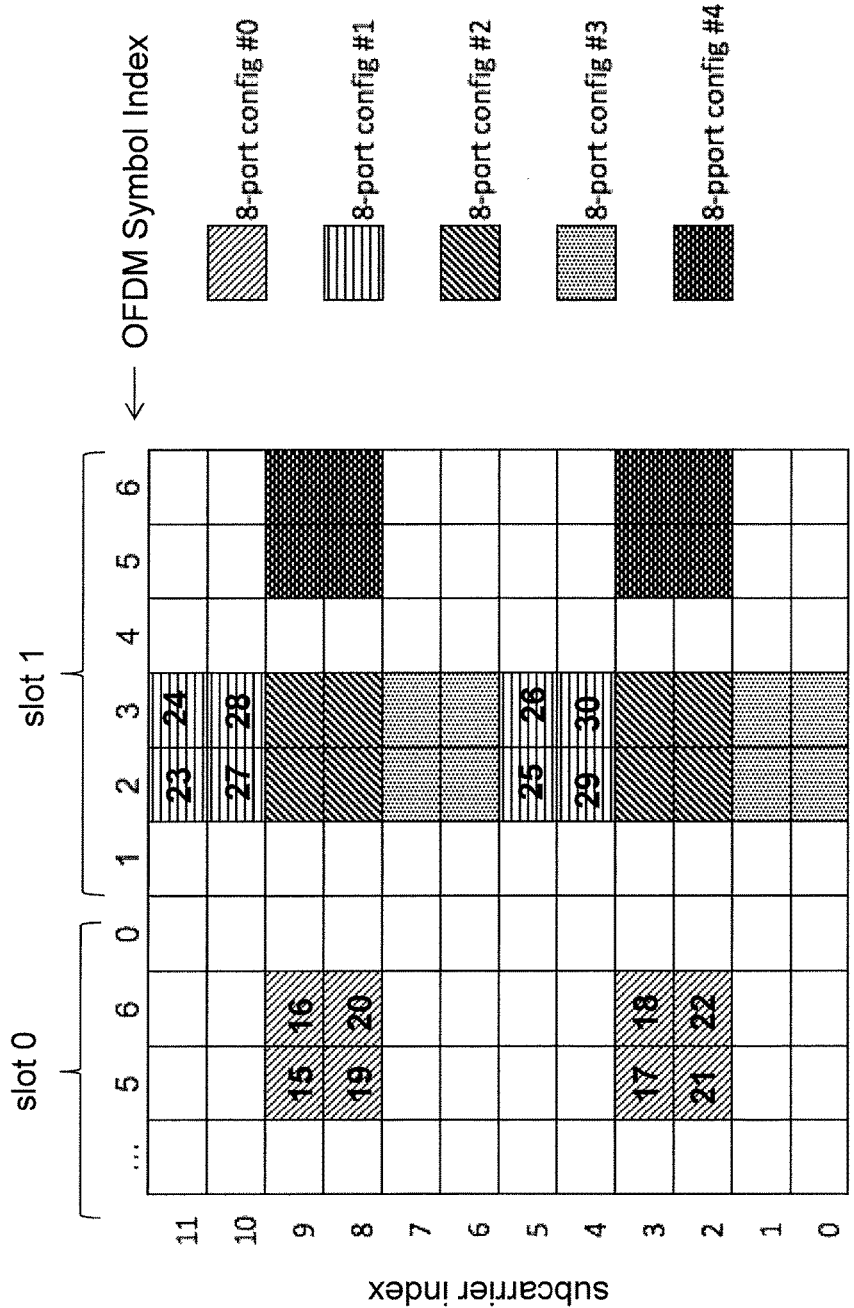
FIG. 15 illustrates legacy 8-port CSI-RS configurations, in accordance with certain embodiments.

However, the Q CSI-RS ports defined in this way may not always correspond to a resource mapping that exists for a CSI resource of Q ports among the legacy CSI-RS resources. For example, FIG. 14 illustrates an example of a 16-port CSI-RS configuration with aggregation of 8 legacy 2-port CSI-RS configurations (i.e., N=2, K=8), in accordance with certain embodiments. By contrast, FIG. 15 illustrates legacy 8-port CSI-RS configurations, in accordance with certain embodiments. If K=8, N=2 CSI resource of the second type is configured for 16 ports as shown in FIG. 14, and Q=8 ports is desired for the first type of resource, aggregation of arbitrary four 2-port CSI-RS configurations may not have the same resource as that of the legacy 8 ports CSI-RS shown in FIG. 15. Therefore, this embodiment is useful for periodic CSI reporting by new Rel-13 wireless devices 110 but not necessarily for legacy wireless devices that are not aware of the new design. If this is desirable, then the solution in embodiment 2 can be applied.

Figure 16:
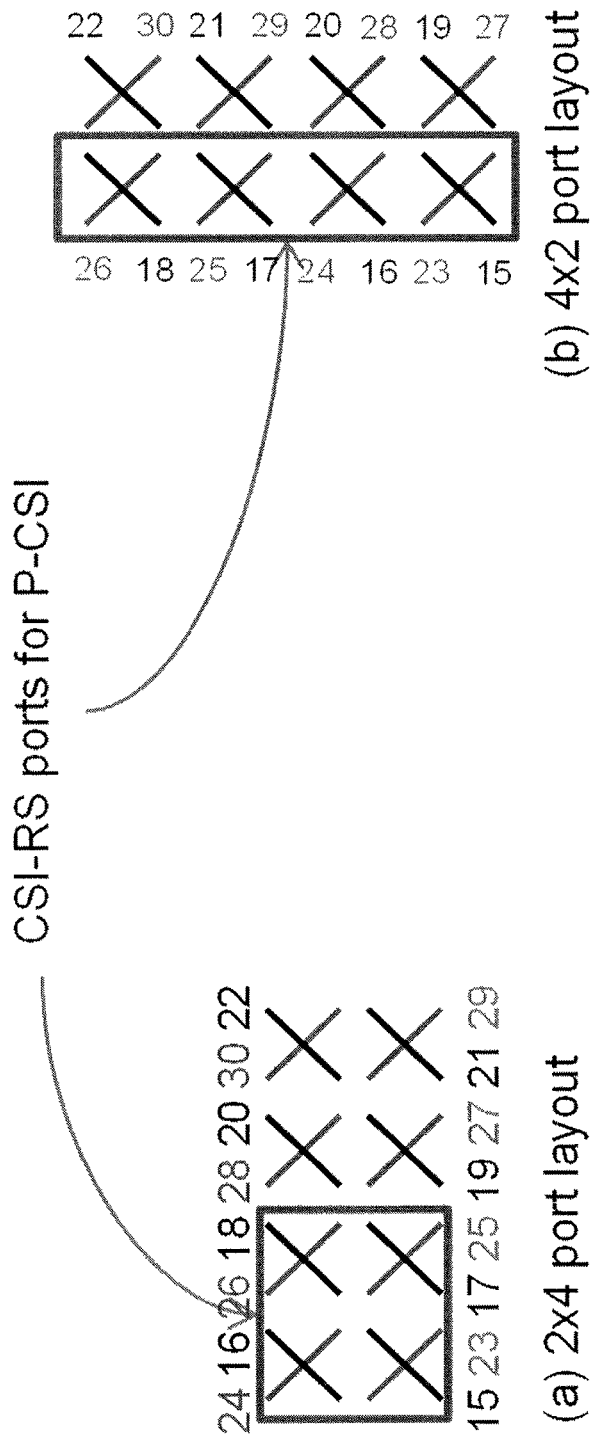
FIG. 16 illustrates the selected CSI-RS ports for the first type of CSI reporting, in accordance with certain embodiments.

FIG. 16 illustrates the selected CSI-RS ports for the first type of CSI reporting, in accordance with certain embodiments. More particularly, FIG. 16 illustrates the selected CSI-RS ports for P-CSI reporting in case of 2×4 and 4×2 antenna port layout (i.e., M1×M2).

In the first particular embodiment described above, CSI measurement of a first type of report was performed over the CSI-RS ports from multiple, or all, of the aggregated CSI-RS resources used in the second type of report. According to a second particular embodiment, the ports related to the first type are confined to a single CSI-RS configuration of the multiple aggregated configurations configured for the second type of CSI measurement and resource. When numbering the antenna ports for the second type of reporting, having P>8 CSI-RS ports, then the following expression is used:

$$p = \begin{cases} r+\frac{N}{2}k & r = 15, 16, \ldots, 14+\frac{N}{2} \\ r+\frac{N}{2}(k+K-1) & r = 15+\frac{N}{2}, \ldots, 14+N \end{cases}$$

where k (=0, ..., K−1) correspond to the k-th CSI-RS configuration (each having N ports). This is the same as that in the first embodiment, and each of the K CSI-RS configurations are mapped to cross-polarized antennas wherein the first half of ports are mapped to one polarization and the second half to the alternate polarization.

For example, if N=8, K=2, P=16, then the ports for the k=0 configuration are numbered as {15,16,17,18,23,24,25, 26}. Now, the ports 15-22 are mapped to antennas of the first polarization and ports 23-30 are mapped to antennas of the second polarization.

Again, since CSI report of the first type such as legacy wireless devices 110, or PUCCH for Release 13 wireless devices 110, need to map to Q ports where Q/2 first ports are co-polarized, and last Q/2 ports also are co-polarized (but with orthogonal polarization), the following port selection for the first type of CSI report is proposed in this embodiment to use the first (i.e., k=0) N CSI-RS ports for measurements and reports of the first type (i.e., Q=N). Or alternatively, to use a predefined configuration (e.g., k=0, or k=1) of the K configurations assigned to the second type of reporting, for measurements and reports of the first type.

In comparison, to the first particular embodiment described above, the number of ports of the first type can be changed depending on the value N used per aggregated configuration in the configuration of the second type. More importantly, the ports of the first type have the same CSI-RS resource as that for a legacy CSI-RS configuration with N ports, and these N ports from a single resource contain a complete set of cross-polarized antennas as legacy N ports. Therefore, a legacy wireless device 110 can be configured with Q=N CSI-RS ports and perform CSI measurement and report according to pre-Release 13 procedures. A Release 13 wireless device 110 can also perform periodic CSI measurement and report with the selected Q CSI-RS ports according to pre-Release 13 procedures.

An example of the subset of CSI-RS ports selected in this embodiment for CSI reporting of the first type and/or for CSI reporting by a legacy wireless device 110 is shown in Table 4 below.

TABLE 4

Examples of CSI-RS ports used for P-CSI measurement and report: M = N

| $M_1$ | $M_2$ | P | N | K | Q | Subset of CSI-RS ports for first type of reporting among ports used for second type of reporting | Port numbering for first type of reporting |
|---|---|---|---|---|---|---|---|
| 8 | 1 | 16 | 8 | 2 | 8 | 15, 16, 17, 18, 23, 24, 25, 26 | 15, 16, 17, 18, 19, 20, 21, 22 |
| 6 | 1 | 12 | 4 | 3 | 4 | 15, 16, 21, 22 | 15, 16, 17, 18 |
| 4 | 2 | 16 | 8 | 2 | 8 | 15, 16, 17, 18, 23, 24, 25, 26 | 15, 16, 17, 18, 19, 20, 21, 22 |
| 2 | 4 | 16 | 2 | 8 | 2 | 15, 23 | 15, 16 |
| 3 | 2 | 12 | 4 | 3 | 4 | 15, 16, 21, 22 | 15, 16, 17, 18 |
| 2 | 3 | 12 | 2 | 6 | 2 | 15, 21 | 15, 16 |

Figure 17:
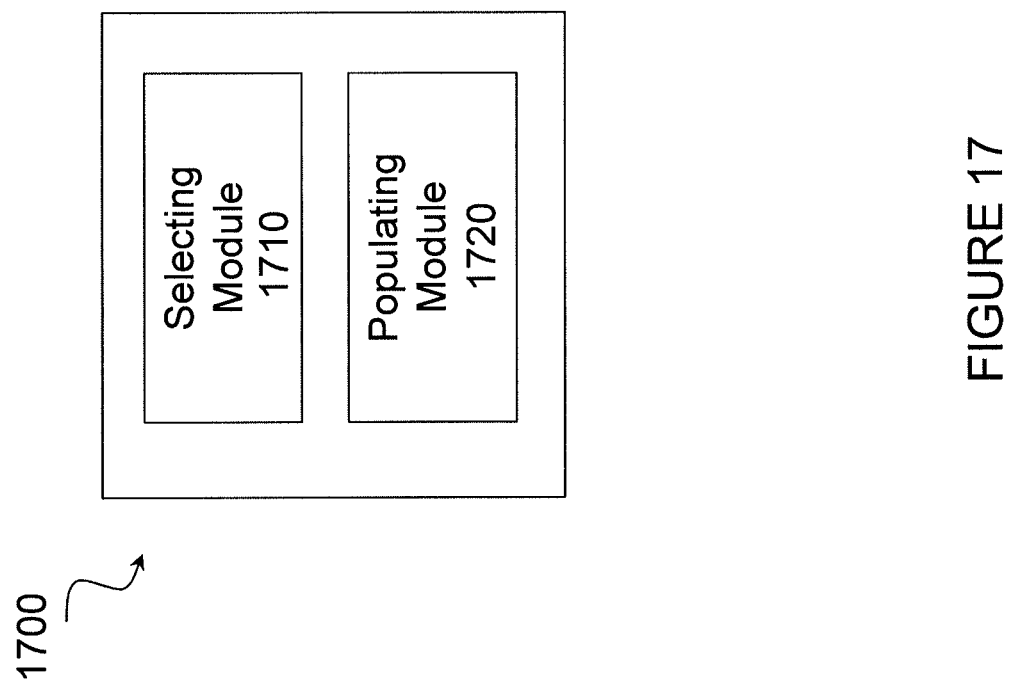
FIG. 17 illustrates an example computer networking virtual apparatus for selecting and populating CSI-RS ports for receiving channel information, according to certain embodiments.

In certain embodiments, the method for selecting and populating CSI-RS ports for receiving channel information as described above may be performed by a computer networking virtual apparatus. FIG. 17 illustrates an example computer networking virtual apparatus 1700 for selecting and populating CSI-RS ports for receiving channel information, according to certain embodiments. In certain embodiments, virtual computing device 1700 may include modules for performing steps similar to those described above with regard to the method illustrated and described in FIG. 11. For example, computer networking virtual apparatus 1700 may include a selecting module 1710, a populating module 1720, and any other suitable modules for selecting and populating CSI-RS ports for receiving channel information. In some embodiments, one or more of the modules may be implemented using one or more processors 1020 of FIG. 10. In certain embodiments, the functions of two or more of the various modules may be combined into a single module.

The selecting module 1710 may perform the selecting functions of computer networking virtual apparatus 1700. For example, selecting module 1710 may select a subset from a predetermined set of P CSI-RS ports for receiving channel information. Each CSI-RS port may correspond to a combination of a set of resource elements and an antenna port of an antenna array. The predetermined set may include a first number $P_1$ of CSI-RS ports with a first polarization state and a second number $P_2$ of CSI-RS ports with a second polarization state, where the first and second polarization states are distinct, in certain embodiments.

The populating module 1720 may perform the populating functions of computer networking virtual apparatus 1700. For example, populating module 1720 may populate the subset with Q CSI-RS ports in such manner that the ratio of CSI-RS ports respectively having the first and second polarization states is equal to the ratio of the first and second numbers. In certain embodiments, the subset may be populated with $QP_1/(P_1+P_2)$ CSI-RS ports having the first polarization state and $QP_2/(P_1+P_2)$ CSI-RS ports having the second polarization state. In certain embodiments, $P_1$ and $P_2$ may be equal. In certain embodiments, half of the CSI-RS ports in the subset may have the first polarization state and half of the CSI-RS ports in the subset have the second polarization state.

Other embodiments of computer networking virtual apparatus 1700 may include additional components beyond those shown in FIG. 17 that may be responsible for providing certain aspects of the functionality of network node 115, including any of the functionality described above and/or any additional functionality (including any functionality necessary to support the solutions described above). The various different types of network nodes 115 may include components having the same physical hardware but configured (e.g., via programming) to support different radio access technologies, or may represent partly or entirely different physical components.

Figure 18:
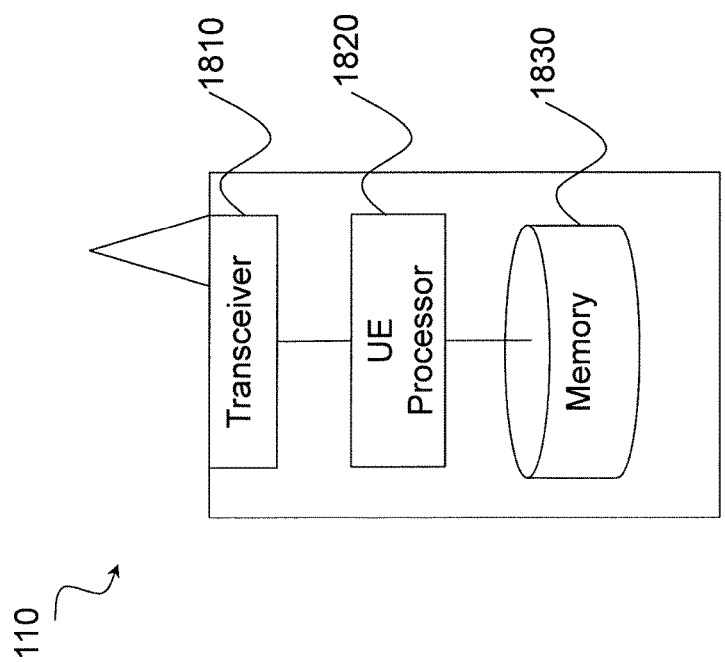
FIG. 18 illustrates an exemplary wireless device, in accordance with certain embodiments.

FIG. 18 is a block schematic of an exemplary wireless device 110, in accordance with certain embodiments. Wireless device 110 may refer to any type of wireless device communicating with a node and/or with another wireless device in a cellular or mobile communication system. As depicted, wireless device 110 includes transceiver 1810, processor 1820, and memory 1830. In some embodiments, transceiver 1810 facilitates transmitting wireless signals to and receiving wireless signals from network node 115 (e.g., via an antenna), processor 1820 executes instructions to provide some or all of the functionality described above as being provided by wireless device 110, and memory 1830 stores the instructions executed by processor 1820. Examples of a network node 115 are provided above.

Processor 1820 may include any suitable combination of hardware and software implemented in one or more modules to execute instructions and manipulate data to perform some or all of the described functions of wireless device 110. In some embodiments, processor 1820 may include, for example, one or more computers, one or more central processing units (CPUs), one or more microprocessors, one or more applications, and/or other logic.

Memory 1830 is generally operable to store instructions, such as a computer program, software, an application including one or more of logic, rules, algorithms, code, tables, etc. and/or other instructions capable of being executed by a processor. Examples of memory 1830 include computer memory (for example, Random Access Memory (RAM) or Read Only Memory (ROM)), mass storage media (for example, a hard disk), removable storage media (for example, a Compact Disk (CD) or a Digital Video Disk (DVD)), and/or or any other volatile or non-volatile, non-transitory computer-readable and/or computer-executable memory devices that store information.

Other embodiments of wireless device 110 may include additional components beyond those shown in FIG. 18 that may be responsible for providing certain aspects of the wireless device's functionality, including any of the functionality described above and/or any additional functionality (including any functionality necessary to support the solution described above).

Figure 19:
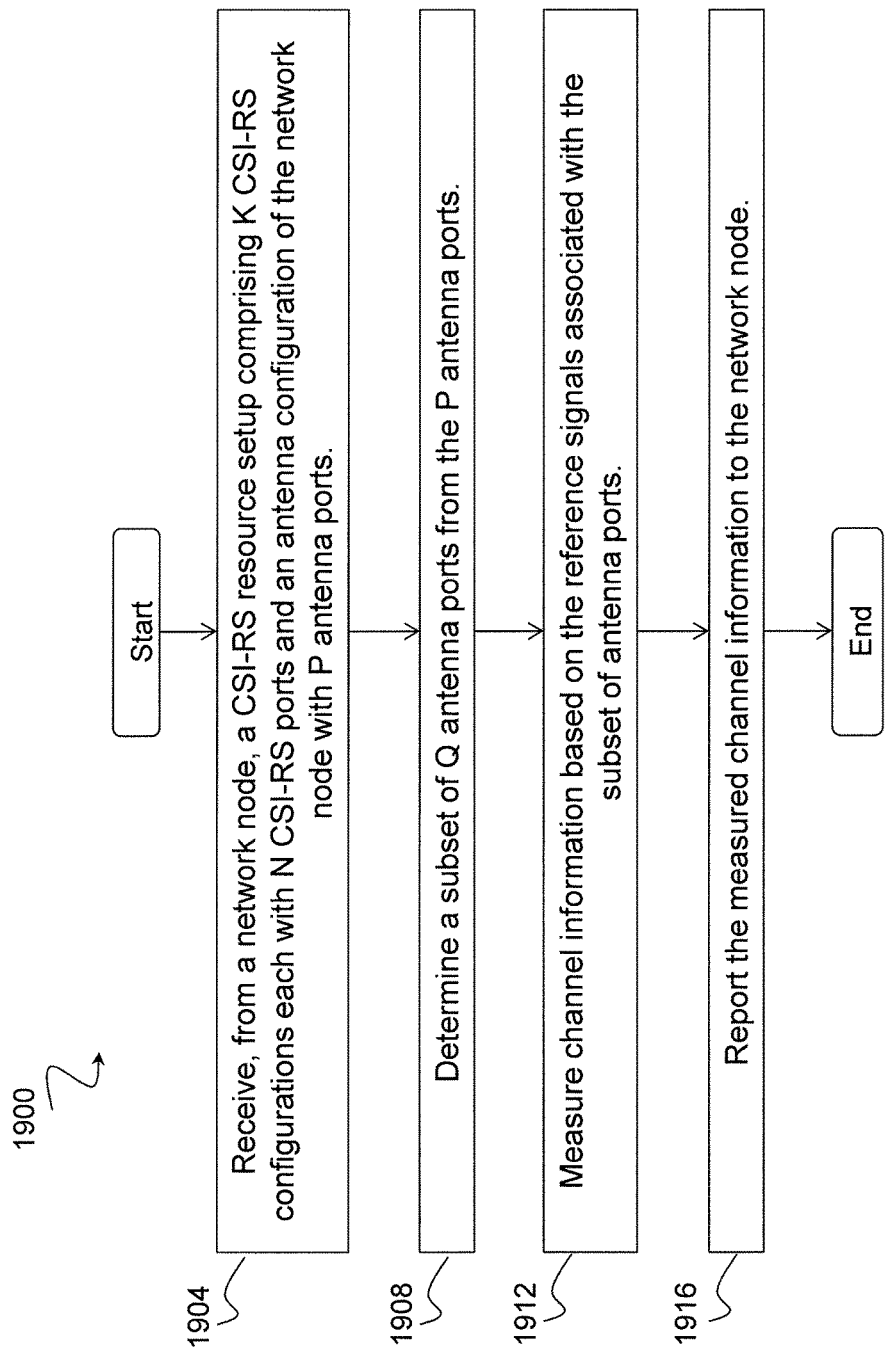
FIG. 19 is a flow diagram of a method in a user equipment, in accordance with certain embodiments.

FIG. 19 is a flow diagram of a method in a wireless device 110, in accordance with certain embodiments. In certain embodiments, wireless device 110 is served by a network node 115 equipped with more than eight antenna ports for transmitting signals to wireless device 110 within a wireless communication network. The method begins at step 1904, when wireless device 110 receives a CSI-RS setup from network node 115. The CSI-RS setup comprises K CSI-RS configurations each with N (legacy) CSI-RS ports and an antenna configuration of the network node with P antenna ports. In a particular embodiment, for example, the antenna configuration includes P CSI-RS ports.

At step 1908, wireless device 110 determines a subset of Q antenna ports from the P antenna ports. In a particular embodiment, for example, a first subset of P/2 CSI-RS ports and a second subset of P/2 CSI-RS ports may be determined from the P CSI-RS ports. The first subset may include N/2 CSI-RS ports from each of the K CSI-RS configurations, and the second subset may include the remaining N/2 CSI-RS ports from each of the K CSI-RS configurations. In a particular embodiment, the first subset may correspond to a first length-P/2 vector of a length-P precoding vector in a codebook used for state information feedback. By contrast, the second subset may correspond to a second length-P/2 vector of the same length-P precoding vector, wherein the second length-P/2 vector is obtainable by scaling the first length-P/2 vector by a complex number.

In certain embodiments, determining the subset of Q antenna ports from the P antenna ports at step 1908 may include forming the first subset as CSI-RS ports indexed by $$p = r + \frac{N}{2}k \quad r = 15, 16, \ldots, 14 + \frac{N}{2},$$

Conversely, the second subset may be formed as CSI-RS ports indexed by $$p = r + \frac{N}{2}(k + K - 1); \quad r = 15 + \frac{N}{2}, \ldots, 14 + N.$$

In both subsets, k may run over the K CSI-RS configuration, k=0, 1, . . . , K−1.

At step 1912, wireless device 110 measures channel information based on the reference signals associated with the subset of antenna ports. For example, the channel information may be estimated over received reference signals associated with the subset of ports based on a predefined codebook of Q ports, in a particular embodiment. Additionally, the measuring of channel information may be performed periodically, in certain embodiments.

At step 1916, wireless device 110 reports the measured channel information to the network node 115. For example, estimated channel information may be sent to the network node 115 over a regular physical uplink control channel, in a particular embodiment. Additionally, the reporting of channel information may be performed periodically, in certain embodiments.

Figure 20:
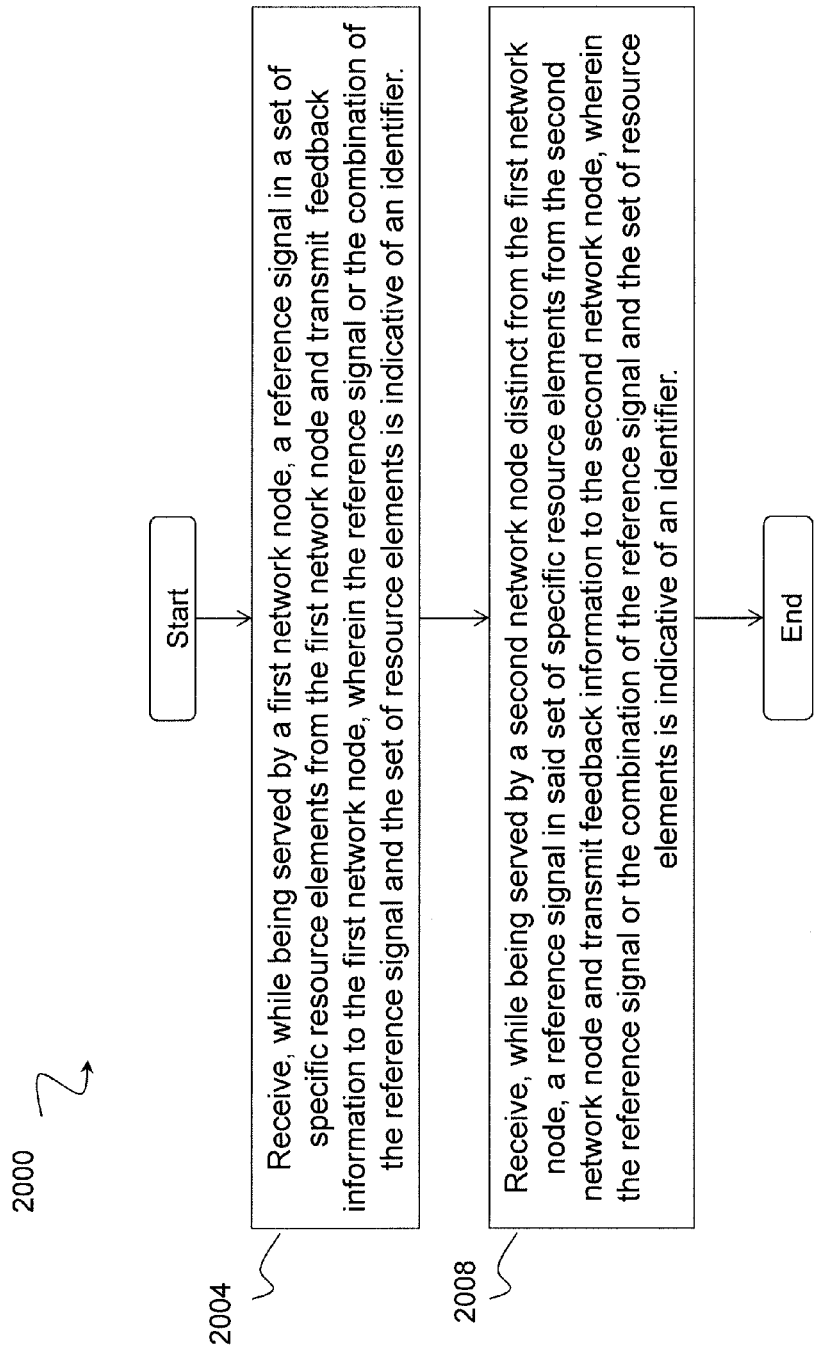
FIG. 20 is a flow diagram of a method in a user equipment, in accordance with certain embodiments.

FIG. 20 is a flow diagram of a method 2000 in a wireless device 110, in accordance with certain embodiments. The method begins at step 2004, when, while being served by a first network node 115, a wireless device 110 receives a reference signal in a specific set of resource elements from the first network node 115 and transmits feedback information to the first network node 115, wherein the reference signal or the combination of the reference signal and the set of resource elements is indicative of an identifier.

At step 2008, while being served by a second network node 115 distinct from the first network node 115, wireless device 110 receives a reference signal in said specific set of resource elements from the second network node 115 and transmits feedback information to the second network node 115. The reference signal or the combination of the reference signal and the set of resource elements is indicative of an identifier.

Figure 21:
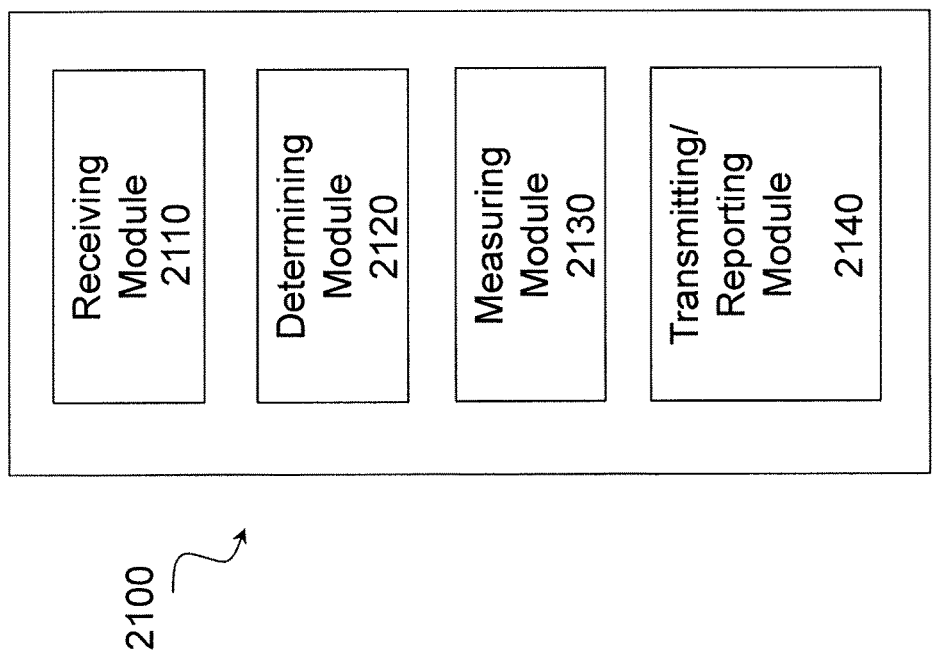
FIG. 21 illustrates an example computer networking virtual apparatus for reporting channel information, according to certain embodiments.

In certain embodiments, the method for providing channel information as described above may be performed by a computer networking virtual apparatus. FIG. 21 illustrates an example computer networking virtual apparatus 2100 for providing channel information, according to certain embodiments. In certain embodiments, virtual computing device 2100 may include modules for performing steps similar to those described above with regard to the methods illustrated and described in FIGS. 19 and 20. For example, computer networking virtual apparatus 2100 may include a receiving module 2110, a determining module 2120, a measuring module 2130, a transmitting and/or reporting module 2140, and any other suitable modules for providing channel information. In some embodiments, one or more of the modules may be implemented using one or more processors 1820 of FIG. 18. In certain embodiments, the functions of two or more of the various modules may be combined into a single module.

The receiving module 2110 may perform the receiving functions of computer networking virtual apparatus 2100. For example, in certain embodiments, receiving module 2110 may receive a CSI-RS setup from a network node. The CSI-RS setup may include K-CSI-RS configurations, each with N CSI-RS ports and an antenna configuration of the network node with P antenna ports.

As another example, in certain embodiments, receiving module 2110 may receive a reference signal in a specific set of resource elements from the first network node 115. The reference signal from the first network node or the combination of the reference signal and the set of resource elements are indicative of an identifier. Receiving module 2110 may also receive a reference signal in said set of specific resource elements from a second network node while being served by the second network node 115. Likewise, the reference signal from the second network node or the combination of the reference signal and the set of resource elements are also indicative of an identifier. The reference signals may be received with different beamforming in spite of the equality of the identifiers.

The determining module 2120 may perform the determining functions of computer networking virtual apparatus 2100. For example, determining module 2100 may determine a subset of Q antenna ports from the P antenna ports received by receiving module 2110, in certain embodiments.

The measuring module 2130 may perform the measuring functions of computer networking virtual apparatus 2100. For example, measuring module 2130 may measure channel information based on the reference signals associated with the subset of antenna ports. In a particular embodiment, the measuring module 2130 may perform the measuring periodically.

The transmitting and/or reporting module 2140 may perform the transmitting and/or reporting functions of computer networking virtual apparatus 2100. For example, in certain embodiments, transmitting and/or reporting module 2140 may report the measured channel information to the network node. In a particular embodiment, the transmitting and/or reporting module 2140 may perform the reporting function periodically.

In certain embodiments, transmitting and/or reporting module 2140 may transmit feedback information to the first network node 115. Additionally or alternatively, transmitting and/or reporting module 2140 may transmit feedback information to the second network node 115.

Other embodiments of computer networking virtual apparatus 2100 may include additional components beyond those shown in FIG. 21 that may be responsible for providing certain aspects of the wireless device's 110 functionality, including any of the functionality described above and/or any additional functionality (including any functionality necessary to support the solutions described above). The various different types of wireless devices 110 may include components having the same physical hardware but configured (e.g., via programming) to support different radio access technologies, or may represent partly or entirely different physical components.

Figure 22:
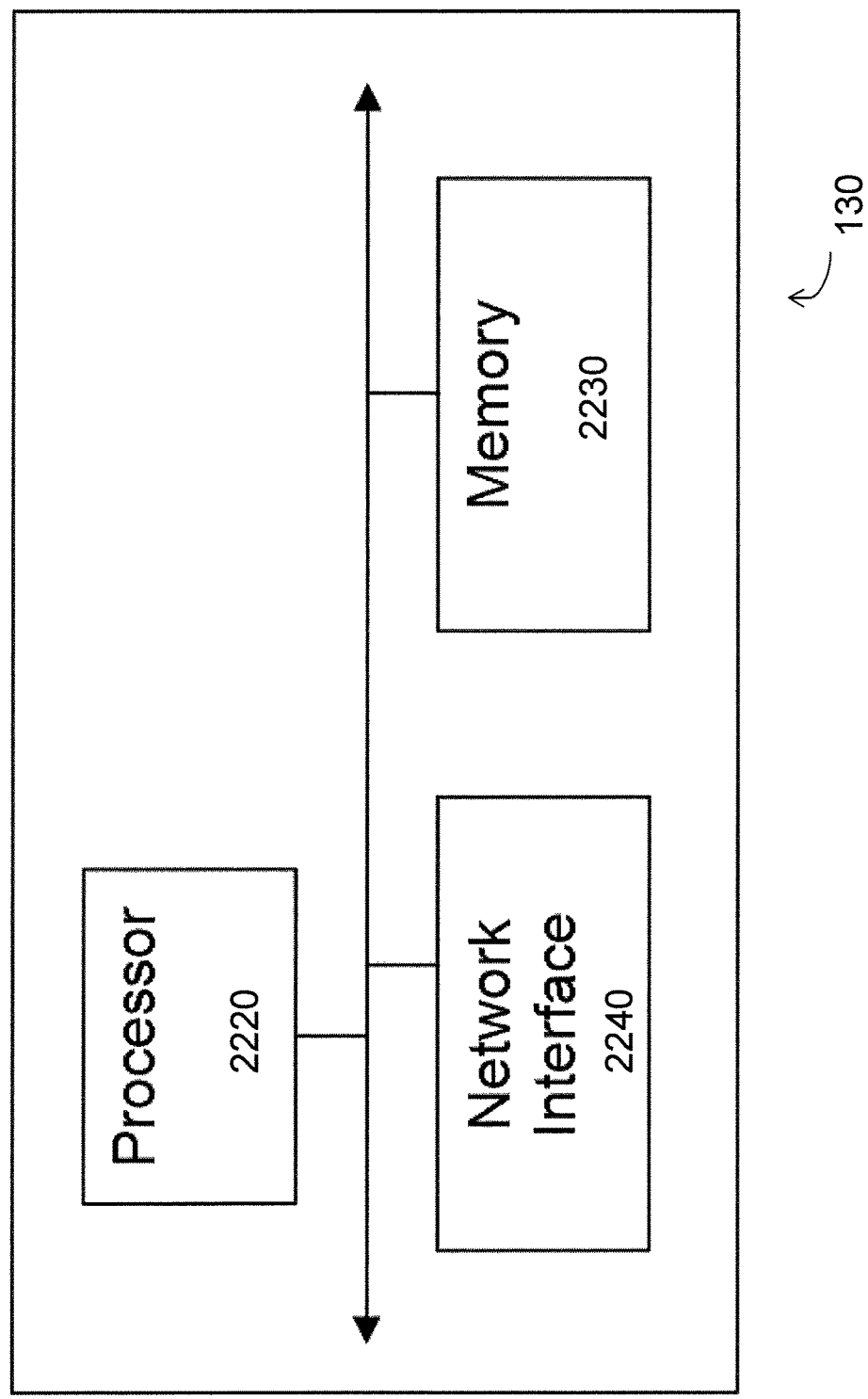
FIG. 22 is a block schematic of an exemplary radio network controller or core network node, in accordance with certain embodiments.

FIG. 22 is a block schematic of an exemplary radio network controller or core network node 130, in accordance with certain embodiments. Examples of network nodes can include a mobile switching center (MSC), a serving GPRS support node (SGSN), a mobility management entity (MME), a radio network controller (RNC), a base station controller (BSC), and so on. The radio network controller or core network node 130 include processor 2220, memory 2230, and network interface 2240. In some embodiments, processor 2220 executes instructions to provide some or all of the functionality described above as being provided by the network node, memory 2230 stores the instructions executed by processor 2220, and network interface 2240 communicates signals to any suitable node, such as a gateway, switch, router, Internet, Public Switched Telephone Network (PSTN), network nodes 115, radio network controllers or core network nodes 130, etc.

Processor 2220 may include any suitable combination of hardware and software implemented in one or more modules to execute instructions and manipulate data to perform some or all of the described functions of the radio network controller or core network node 130. In some embodiments, processor 2220 may include, for example, one or more computers, one or more central processing units (CPUs), one or more microprocessors, one or more applications, and/or other logic.

Memory 2230 is generally operable to store instructions, such as a computer program, software, an application including one or more of logic, rules, algorithms, code, tables, etc. and/or other instructions capable of being executed by a processor. Examples of memory 2230 include computer memory (for example, Random Access Memory (RAM) or Read Only Memory (ROM)), mass storage media (for example, a hard disk), removable storage media (for example, a Compact Disk (CD) or a Digital Video Disk (DVD)), and/or any other volatile or non-volatile, non-transitory computer-readable and/or computer-executable memory devices that store information.

In some embodiments, network interface 2240 is communicatively coupled to processor 2220 and may refer to any suitable device operable to receive input for the network node, send output from the network node, perform suitable processing of the input or output or both, communicate to other devices, or any combination of the preceding. Network interface 2240 may include appropriate hardware (e.g., port, modem, network interface card, etc.) and software, including protocol conversion and data processing capabilities, to communicate through a network.

Other embodiments of the network node may include additional components beyond those shown in FIG. 22 that may be responsible for providing certain aspects of the network node's functionality, including any of the functionality described above and/or any additional functionality (including any functionality necessary to support the solution described above).

According to certain embodiments, a method of selecting a subset from a predetermined set of P CSI-RS ports for receiving channel state information is provided. The method is implemented in a network node (115) of a wireless communication network (100). The network node comprises an antenna array with controllable polarization. Each CSI-RS port corresponds to a combination of a set of resource elements and an antenna port of said antenna array. The predetermined set comprises a first number $P_1$ of CSI-RS ports with a first polarization state and a second number $P_2$ of CSI-RS ports with a second polarization state, where the first and second polarization states distinct. The method includes populating the subset with Q CSI-RS ports in such manner that the ratio of CSI-RS ports respectively having the first and second polarization states is equal to the ratio of the first and second numbers.

Optionally, The subset is populated with $QP_1/(P_1+P_2)$ CSI-RS ports having the first polarization state and $QP_2/(P_1+P_2)$ CSI-RS ports having the second polarization state.

Optionally, $P_1=P_2$, whereby the subset is populated with equal proportions of CSI-RS ports with the first and second polarization states.

Optionally, $P_1+P_2=P$.

Optionally, half of the CSI-RS ports in the subset have the first polarization state and half of the CSI-RS ports in the subset have the second polarization state.

Optionally, $Q \leq 8$.

Optionally, Q is a multiple of 2.

Optionally, Q=2 or Q=4 or Q=8.

Optionally, each CSI-RS port in the predetermined set is associated with an identifier susceptible of enabling the network node to identify feedback relating to a reference signal transmitted by the network node on this CSI-RS port.

Optionally, one of the following holds: the identifier is explicitly stated in a feedback signal; the identifier is implicitly derivable from an internal structure of a feedback signal; and the identifier is implicitly derivable from a resource used for transmitting a feedback signal.

Optionally, the CSI-RS ports are selected from an ordered set.

Optionally, the ordered set is one of a subset of the integers or a subset of an alphabet.

Optionally, populating the subset includes preserving the identifiers with which the CSI-RS ports are associated.

Optionally, the CSI-RS ports with a first polarization state are associated with identifiers in a first predetermined range, and the CSI-RS ports with a second polarization state are associated with identifiers in a second predetermined range. The subset is populated with Q/2 CSI-RS ports from a lower portion of the first predetermined range and Q/2 CSI-RS ports from a lower portion of the second predetermined range.

Optionally, each CSI-RS port is associated with an identifier being a port number p given by $$p = \begin{cases} r + \frac{N}{2}k & r = 15, 16, \ldots, 14 + \frac{N}{2} \\ r + \frac{N}{2}(k + K - 1) & r = 15 + \frac{N}{2}, \ldots, 14 + N \end{cases}$$

where K is a number of CSI reference signal configurations, k is any integer in $[0, K-1]$, N is the number of antenna ports or reference signals in each of the K configurations, and r is any integer in $[15, 14+N]$.

Optionally, the subset is populated with Q CSI-RS ports associated with port numbers given by $$p = \begin{cases} r + \frac{N}{2}k & r = 15, 16, \ldots, 14 + \frac{N}{2} \\ r + \frac{N}{2}(k + K - 1) & r = 15 + \frac{N}{2}, \ldots, 14 + N \end{cases}$$

where k is restricted to $$\left[0, \frac{Q}{N} - 1\right] \text{ and } Q \geq N.$$

Optionally, the CSI-RS ports are associated with alternative identifiers, which are selected from the ordered set and susceptible of enabling the network node to identify a first type of feedback relating to a CSI reference signal transmitted by the network node on a CSI-RS port.

Optionally, the identifiers define an ordering of the CSI-RS ports, which is preserved by the alternative identifiers.

Optionally, the alternative identifiers are consecutive.

Optionally, the alternate identifiers p' are given by $$p' = \begin{cases} p, & q = 0; \\ p - \frac{KN - Q}{2}, & q = 1. \end{cases}$$

where q=0 is for the first polarization state and q=1 is for the second polarization state.

Optionally, an aggregated resource and port number are assigned to each CSI-RS port in the subset.

Optionally, the number Q of CSI-RS ports in the subset is determined as a function of the number P of CSI-RS ports in the predetermined set.

Optionally, determining includes one of: selecting $Q \leq 8$ such that $Q<P$; selecting $Q \in \{2, 4, 8\}$ such that $Q<P$; selecting a greatest possible $Q \leq 8$ such that $Q<P$; and selecting a greatest possible $Q \in \{2, 4, 8\}$ such that $Q<P$.

Optionally, the method is implemented in a network node comprising an antenna array with antenna elements arranged along two axes.

Optionally, the first polarization state corresponds to a linear array of antenna elements with one polarization direction and the second polarization state corresponds to a linear array of antenna elements with a second polarization direction.

Optionally, the antenna array comprises cross-polarized antenna elements.

Optionally, the method further includes transmitting a plurality of CSI reference signals over CSI-RS ports from the predetermined set and receiving feedback from a user equipment (110) in the wireless communication network.

Optionally, the method further includes determining whether feedback of a first or second type is to be enabled. If feedback of the first type is to be enabled, transmitting reference signals on CSI-RS ports from the subset. If feedback of the second type is to be enabled, transmitting reference signals on CSI-RS ports from the predetermined set.

Optionally, the method further includes using a common codebook for both types of reporting.

Optionally, the method further includes using a first codebook for the first type of reporting and a second codebook for the second type of reporting.

Optionally, the first type of feedback is periodic CSI reporting.

Optionally, the method further includes an initial step of signaling to the user equipment a number P of antenna ports by which the network node is configured and signaling a configuration of CSI-RS ports corresponding to the total of P CSI-RS ports being K aggregated N-port CSI-RS configurations, where K is the number of available CSI reference signal configurations.

According to certain embodiments, a method in a user equipment (110) operable in a wireless communication network (100), operable to be served by a plurality of network nodes (115), each of which comprises an antenna array is provided. The method includes, while being served by a first network node (115A), receiving a reference signal in a specific set of resource elements from the first network node and transmitting feedback information to the first network node. The reference signal or the combination of the reference signal and the set of resource elements is indicative of an identifier. While being served by a second network node (115B) distinct from the first network node, a reference signal in said set of specific resource elements is received from the second network node, and feedback information is transmitted to the second network node. The reference signal or the combination of the reference signal and the set of resource elements is indicative of an identifier, wherein the reference signal is received with different beamforming from the first and second network nodes in spite of equality of the identifiers.

According to certain embodiments, a method in a user equipment (110) is served by a wireless communication network node (115) equipped with more than eight antenna ports for transmitting signals to the UE. The method includes receiving, from the network node, a CSI-RS configuration comprising K CSI-RS configurations each with N CSI-RS ports and an antenna configuration of the network node with P antenna ports. A subset of Q antenna ports is determined from the P antenna ports. Channel state information is periodically measured based on the reference signals associated the subset of antenna ports. The measured channel state information is periodically reported to the network node.

According to certain embodiments, a method in a network node is disclosed. The method comprises selecting a subset from a predetermined set of P CSI-RS ports for receiving channel information. The network node comprises an antenna array with controllable polarization. Each CSI-RS port corresponds to a combination of a set of resource elements and an antenna port of said antenna array. The predetermined set comprises a first number $P_1$ of CSI-RS ports with a first polarization state and a second number $P_2$ of CSI-RS ports with a second polarization state. The first and second polarization states are distinct. The method further comprises populating the subset with Q CSI-RS ports in such manner that the ratio of CSI-RS ports respectively having the first and second polarization states is equal to the ratio of the first and second numbers.

According to certain embodiments, a method in a wireless device served by a network node of a wireless communication network is provided. The network node is equipped with P=8 or P>8 antenna ports for transmitting signals to the wireless device. The method includes receiving, from the network node, a CSI-RS setup that includes K CSI-RS configurations each with N CSI-RS ports and an antenna configuration of the network node with P antenna ports. A subset of Q antenna ports is determined from the P antenna ports. Channel information is measured based on the reference signals associated with the subset of antenna ports. The measure channel information is reported to the network node.

According to certain embodiments, a method in a wireless device of a wireless communication network is provided. The wireless device is served by a plurality of network nodes, and each network node includes an antenna array. The method includes receiving a reference signal in a specific set of resource elements from a first network node while being served by the first network node. Feedback information is transmitted to the first network node. The reference signal or the combination of the reference signal and the set of resource elements is indicative of an identifier. While being served by a second network node distinct from the first network node, a reference signal in said set of specific resource elements is received from the second network node. Feedback information is transmitted to the second network node, and the reference signal or the combination of the reference signal and the set of resource elements is indicative of an identifier. The reference signal is received with different beamforming from the first and second network nodes in spite of the equality of the identifiers.

According to certain embodiments, a network node is provided. The network node includes an antenna array with controllable polarization, and one or more processors. The one or more processors are configured to select a subset from a predetermined set of P CSI-RS ports for receiving channel information, wherein each CSI-RS port corresponds to a combination of a set of resource elements and an antenna port of said antenna array, the predetermined set comprises a first number $P_1$ of CSI-RS ports with a first polarization state and a second number $P_2$ of CSI-RS ports with a second polarization state, the first and second polarization states being distinct. The one or more processors are further configured to populate the subset with Q CSI-RS ports in such manner that the ratio of CSI-RS ports respectively having the first and second polarization states is equal to the ratio of the first and second numbers.

According to certain embodiments, a wireless device configured to be served by a network node in a wireless communication network is provided. The network node is equipped with P=8 or P>8 antenna ports for transmitting signals to the wireless device. The wireless device includes one or more processors. The one or more processors are configured to receive, from the network node, a CSI-RS set up comprising K CSI reference signal configurations each with N CSI-RS ports and an antenna configuration of the network node with P antenna ports. The one or more processors are further configured to determine a subset of Q antenna ports from the P antenna ports and measure channel information based on the reference signals associated with the subset of antenna ports. The measured channel information is reported to the network node.

According to certain embodiments, a wireless device configured to be served by a plurality of network nodes each comprising an antenna array is provided. The wireless device includes one or more processors. The one or more processors are configured to, while being served by a first network node, receive a reference signal in a specific set of resource elements from the first network node and transmit feedback information to the first network node. The reference signal or the combination of the reference signal and the set of resource elements is indicative of an identifier. The one or more processors are further configured to, while being served by a second network node distinct from the first network node, receive a reference signal in said specific resource element from the second network node and transmit feedback information to the second network node. The reference signal or the combination of the reference signal and the set of resource elements is indicative of an identifier, and the wireless device is configured to receive the reference signal with different beamforming from the first and second network nodes in spite of equality of the identifiers.

According to certain embodiments, a computer program product comprising instructions stored on non-transient computer-readable media which, when executed by a processor, performs the acts of: selecting a subset from a predetermined set of P CSI-RS ports for receiving channel information, wherein each CSI-RS port corresponds to a combination of a set of resource elements and an antenna port of an antenna array, the predetermined set comprises a first number $P_1$ of CSI-RS ports with a first polarization state and a second number $P_2$ of CSI-RS ports with a second polarization state, the first and second polarization states being distinct; and populating the subset with Q CSI-RS ports in such manner that the ratio of CSI-RS ports respectively having the first and second polarization states is equal to the ratio of the first and second numbers.

According to certain embodiments, a computer program product comprising instructions stored on non-transient computer-readable media which, when executed by a processor, performs the acts of: while being served by a first network node, receiving a reference signal in a set of specific resource elements from the first network node and transmitting feedback information to the first network node, wherein the reference signal or the combination of the reference signal and the set of resource elements is indicative of an identifier; and while being served by a second network node distinct from the first network node, receiving a reference signal in said set of specific resource elements from the second network node and transmitting feedback information to the second network node, wherein the reference signal or the combination of the reference signal and the set of resource elements is indicative of an identifier. The reference signal is received with different beamforming from the first and second network nodes in spite of equality of the identifiers.

According to certain embodiments, a computer program product comprising instructions stored on non-transient computer-readable media which, when executed by a processor, performs the acts of:

receiving, from a network node, a CSI-RS setup comprising K CSI reference signal configurations each with N CSI-RS ports and an antenna configuration of the network node with P antenna ports, wherein the network node is equipped with P=8 or P>8 antenna ports for transmitting signals to the wireless device; determining a subset of Q antenna ports from the P antenna ports; measuring channel information based on the reference signals associated the subset of antenna ports; and reporting the measured channel information to the network node.

Certain embodiments of the present disclosure may provide one or more technical advantages. As one example, certain embodiments may advantageously not require additional signaling for configuring CSI-RS ports for periodic CSI reporting. As another example, legacy terminals can be supported with the same eNB antenna array as FD-MIMO supporting terminals without additional CSI-RS overhead, since the ports used for first type of feedback is a subset of the ports used for second type of feedback. As yet another example, the codebooks, which are designed for cross polarized antenna arrays where the first half of antenna ports are on one polarization and the second half of antenna ports are on a different polarization, can be used both for the first type and the second type of feedback.

Modifications, additions, or omissions may be made to the systems and apparatuses described herein without departing from the scope of the disclosure. The components of the systems and apparatuses may be integrated or separated. Moreover, the operations of the systems and apparatuses may be performed by more, fewer, or other components. Additionally, operations of the systems and apparatuses may be performed using any suitable logic comprising software, hardware, and/or other logic. As used in this document, "each" refers to each member of a set or each member of a subset of a set.

Modifications, additions, or omissions may be made to the methods described herein without departing from the scope of the disclosure. The methods may include more, fewer, or other steps. Additionally, steps may be performed in any suitable order.

Although this disclosure has been described in terms of certain embodiments, alterations and permutations of the embodiments will be apparent to those skilled in the art. Accordingly, the above description of the embodiments does not constrain this disclosure. Other changes, substitutions, and alterations are possible without departing from the spirit and scope of this disclosure, as defined by the following claims.

Abbreviations used in the preceding description include:
ARQ Automatic Retransmission Request
CQI Channel Quality Indicators
CSI Channel State Information
CSI-RS Channel State Information Reference Signals
DFT Discrete Fourier Transform
LTE Long Term Evolution
MIMO Multiple Input Multiple Output
OCC Orthogonal Cover Code
OFDM Orthogonal Frequency Division Multiplexing
PMI Precoding Matrix Indicator
PUCCH Physical Uplink Control Channel
RI Rank Indicator
SINR Signal to Interference plus Noise Ratio
TFRE Time Frequency Resource Element
UE User Equipment

The invention claimed is:

1. A method in a network node of a wireless communication network for selecting a subset Channel State Information-Reference Signal (CSI-RS) ports from a predetermined set of P CSI-RS ports for receiving channel information, wherein P is an integer equal to or greater than 2, the method comprising:
operating the network node with an antenna array with a first polarization state and a second polarization state, the first and second polarization states being distinct, wherein:
each CSI-RS port corresponds to a combination of a set of resource elements and an antenna port of said antenna array and is associated with an identifier which is either (a) explicitly stated in a feedback signal, or (b) implicitly derivable from an internal structure of a feedback signal, or (c) implicitly derivable from a resource used for transmitting a feedback signal;
the predetermined set of the CSI-RS ports comprises a first number $P_1$ of CSI-RS ports with the first polarization state associated with identifiers in a first predetermined range and a second number $P_2$ of CSI-RS ports with the second polarization state associated with identifiers in a second predetermined range; and $P_1+P_2=P$;
populating the selected subset of CSI-RS ports with Q CSI-RS ports, Q<P, in such manner that a ratio of numbers of CSI-RS ports having the first and second polarization states is equal to the ratio of the first and second numbers, wherein one of the following holds: (i) the subset is populated with Q/2 CSI-RS ports from a lower portion of the first predetermined range and Q/2 CSI-RS ports from a lower portion of the second predetermined range; (ii) the subset is populated with Q/2 CSI-RS ports from a higher portion of the first predetermined range and Q/2 CSI-RS ports from a higher portion of the second predetermined range;
if feedback of a first type is to be enabled, transmitting reference signals on CSI-RS ports from the subset; and,
if feedback of a second type is to be enabled, transmitting reference signals on CSI-RS ports from the predetermined set.

2. The method of claim 1, wherein the subset is populated with $QP_1/(P_1+P_2)$ CSI-RS ports having the first polarization state and $QP_2/(P_1+P_2)$ CSI-RS ports having the second polarization state.

3. The method of claim 1, wherein $P_1=P_2$, whereby the subset is populated with equal proportions of CSI-RS ports with the first and second polarization states.

4. The method of claim 1, whereby half of the CSI-RS ports in the subset have the first polarization state and half of the CSI-RS ports in the subset have the second polarization state.

5. The method of claim 1, wherein each CSI-RS port is associated with an identifier being a port number p given by $$p = \begin{cases} r + \frac{N}{2}k & r = 15, 16, \ldots, 14 + \frac{N}{2} \\ r + \frac{N}{2}(k+K-1) & r = 15 + \frac{N}{2}, \ldots, 14 + N \end{cases}$$

where K_ is a number of CSI reference signal configurations, k is any integer in [0, K−1], N is an even integer being the number of antenna ports or reference signals in each of the K configurations, and r is any integer in [15, 14+N].

6. The method of claim 5, wherein the subset consists of CSI-RS ports with port numbers given by Eq. 1.

7. The method of claim 5, wherein the subset is populated with Q CSI-RS ports associated with port numbers given by $$p = \begin{cases} r + \frac{N}{2}k & r = 15, 16, \ldots, 14 + \frac{N}{2} \\ r + \frac{N}{2}(k+K-1) & r = 15 + \frac{N}{2}, \ldots, 14 + N \end{cases}$$

where k is restricted to $$\left[0, \frac{Q}{N} - 1\right] \text{ and } Q \geq N.$$

8. The method of claim 1, wherein:
said populating comprises populating the subset with a number of CSI-RS ports from a lower portion of the first predetermined range and an equal number of CSI-RS ports from a lower portion of the second predetermined range, each CSI-RS port in the subset being associated with an identifier that is a port number p given by $$p = \begin{cases} r + \frac{N}{2}k & r = 15, 16, \ldots, 14 + \frac{N}{2} \\ r + \frac{N}{2}(k + K - 1) & r = 15 + \frac{N}{2}, \ldots, 14 + N \end{cases}, \quad \text{(Eq. 1)}$$

where K is a number of CSI reference signal configurations, k is any integer in [0, K−1], N is an even integer being the number of antenna ports or reference signals in each of the K configurations, and r is any integer in [15,14+N].

9. The method of claim 1, further comprising: associating the CSI-RS ports with alternative identifiers, which are selected from the ordered set and susceptible of enabling the network node to identify a first type of feedback relating to a CSI reference signal transmitted by the network node on a CSI-RS port.

10. The method of claim 9, wherein the identifiers define an ordering of the CSI-RS ports, which is preserved by the alternative identifiers.

11. The method of claim 10, wherein the alternative identifiers are consecutive.

12. The method of claim 9, where the alternative identifiers p' are given by $$p' = \begin{cases} p' & q = 0; \\ p - \frac{KN - Q}{2}, & q = 1. \end{cases}$$

where q=0 is for the first polarization state and q=1 is for the second polarization state.

13. The method of claim 1, further comprising:
receiving feedback from a wireless device in the wireless communication network.

14. The method of claim 13, further comprising:
determining whether feedback of a first or second type is to be enabled.

15. The method of claim 1, wherein the CSI-RS ports with the first polarization state differ from the CSI-RS ports with the second polarization state in that a first co-phasing coefficient is applied to the CSI-RS ports with the first polarization state and a distinct second co-phasing coefficient is applied to the CSI-RS ports with the second polarization state.

16. A method for reporting Channel State Information (CSI), the method implemented in a wireless device served by a network node of a wireless communication network, the network node being equipped with P=8 or P>8 antenna ports for transmitting signals to the wireless device, the method comprising:
receiving, from the network node, a Channel State Information-Reference Signal (CSI-RS) setup comprising K CSI-RS configurations, wherein K≥1, and wherein each CSI-RS configuration comprises N CSI-RS ports and an antenna configuration of the network node with P antenna ports, wherein N is defined as 1≤N≤P and is a multiple of 2, and wherein each CSI-RS port is associated with an identifier which is either (a) explicitly stated in a feedback signal, or (b) implicitly derivable from an internal structure of a feedback signal, or (c) implicitly derivable from a resource used for transmitting a feedback signal;
determining a subset of Q antenna ports from the P antenna ports, where Q≤P;
if feedback of a first type is enabled, measuring channel information based on the reference signals associated with the subset of antenna ports;
if feedback of a second type is enabled, measuring channel information based on the reference signals associated with the P antenna ports;
reporting the measured channel information to the network node,
wherein one of the following holds: (i) the subset comprises Q/2 CSI-RS ports from a lower portion of a first predetermined range of identifiers and Q/2 CSI-RS ports from a lower portion of a second predetermined range of identifiers, or (ii) the subset comprises Q/2 CSI-RS ports from a higher portion of the first predetermined range and Q/2 CSI-RS ports from a higher portion of the second predetermined range,
wherein the identifiers in the first and second predetermined ranges are associated with CSI-RS ports with first and second polarization states, respectively.

17. The method of claim 16, wherein:
the antenna configuration of the CSI-RS setup comprises P CSI-RS ports;
said determining a subset of Q ports comprises determining a first subset of P/2 CSI-RS ports and a second subset of P/2 CSI-RS ports from the P CSI-RS ports, wherein:
the first subset comprises N/2 CSI-RS ports from each of the K CSI-RS configurations, where N is an even integer; and
the second subset comprises the remaining N/2 CSI-RS ports from each of the K CSI-RS configurations.

18. The method of claim 17, wherein:
the first subset corresponds to a first length-P/2 vector in a codebook used for state information feedback, the vector being selected from a set of possible values in the codebook;
the second subset corresponds to a second length-P/2 vector obtainable by scaling the first length-P/2 vector by a complex number; and
the first and second length-P/2 vectors are applied to respective sets of co-polarized antennas.

19. The method of claim 17, wherein the determining comprises forming the first subset as CSI-RS ports indexed by $$p = r + \frac{N}{2}k$$
$$r = 15, 16, \ldots, 14 + \frac{N}{2},$$

and forming the second subset as CSI-RS ports indexed by $$p = r + \frac{N}{2}(k + K - 1);$$

-continued $$r = 15 + \frac{N}{2}, \ldots, 14 + N,$$

wherein, for both subsets, k runs over the K CSI-RS configurations such that k=0, 1, . . . K−1.

20. The method of claim 16, wherein the measuring and reporting are performed periodically if feedback of the first type is enabled.

21. The method of claim 16, wherein the determining comprises deriving the Q antenna ports, which ports are indexed by $$p = \begin{cases} r + \frac{N}{2}k & r = 15, 16, \ldots, 14 + \frac{N}{2} \\ r + \frac{N}{2}(k + K - 1) & r = 15 + \frac{N}{2}, \ldots, 14 + N \end{cases}$$

where k is restricted to $$\left[0, \frac{Q}{N} - 1\right],$$

and N is an even integer.

22. The method of claim 21, wherein the indices of the derived Q antenna ports are re-ordered such that the second set of $$\frac{Q}{2}$$

ports $$p = r + \frac{N}{2}(k + K - 1), \text{ where } r = 15 + \frac{N}{2}, \ldots, 14 + N,$$

are re-indexed as ports $$\left\{15 + \frac{Q}{2}, \ldots, 15 + Q\right\},$$

and N is an even integer.

23. A network node comprising:
an antenna array with a first polarization state and a second polarization state, the first and second polarization states being distinct; and
one or more processors configured to:
  select a subset of Channel State Information-Reference Signal (CSI-RS) ports from a predetermined set of P CSI-RS ports for receiving channel information, wherein P is an integer equal to or greater than 2, wherein each CSI-RS port corresponds to a combination of a set of resource elements and an antenna port of said antenna array and is associated with an identifier which is either (a) explicitly stated in a feedback signal, or (b) implicitly derivable from an internal structure of a feedback signal, or (c) implicitly derivable from a resource used for transmitting a feedback signal, the predetermined set of P CSI-RS ports comprises a first number $P_1$ of CSI-RS ports with the first polarization state associated with identifiers in a first predetermined range and a second number $P_2$ of CSI-RS ports with the second polarization state associated with identifiers in a second predetermined range, wherein $P_1+P_2=P$;
  populate the selected subset of CSI-RS ports with Q CSI-RS ports, Q<P, in such manner that a ratio of numbers of CSI-RS ports having the first and second polarization states is equal to the ratio of the first and second numbers, wherein one of the following holds: (i) the subset is populated with Q/2 CSI-RS ports from a lower portion of the first predetermined range and Q/2 CSI-RS ports from a lower portion of the second predetermined range; (ii) the subset is populated with Q/2 CSI-RS ports from a higher portion of the first predetermined range and Q/2 CSI-RS ports from a higher portion of the second predetermined range;
  if feedback of a first type is to be enabled, transmitting reference signals on CSI-RS ports from the subset; and
  if feedback of a second type is to be enabled, transmitting reference signals on CSI-RS ports from the predetermined set.

24. A wireless device configured to be served by a network node of a wireless communication network, the network node being equipped with P antenna ports transmitting signals to the wireless device, the wireless device comprising:
one or more processors, configured to:
  receive, from the network node, a Channel State Information-Reference Signal (CSI-RS) setup comprising K CSI-RS configurations, wherein K≥1 and each CSI-RS configuration comprises N CSI-RS ports and an antenna configuration of the network node with P antenna ports, wherein N is defined as 1≤N≤P and is a multiple of 2, and wherein P≥2, each CSI-RS port associated with an identifier which is either (a) explicitly stated in a feedback signal, or (b) implicitly derivable from an internal structure of a feedback signal, or (c) implicitly derivable from a resource used for transmitting a feedback signal;
  determine a subset of Q antenna ports from the P antenna ports, wherein Q≤P;
  if feedback of a first type is enabled, measure channel information based on the reference signals associated with the subset of antenna ports;
  if feedback of a second type is enabled, measure channel information based on the reference signals associated with the P antenna ports; and
  report the measured channel information to the network node,
wherein one of the following holds: (i) the subset is populated with Q/2 CSI-RS ports from a lower portion of the first predetermined range and Q/2 CSI-RS ports from a lower portion of the second predetermined range; (ii) the subset is populated with Q/2 CSI-RS ports from a higher portion of the first predetermined range and Q/2 CSI-RS ports from a higher portion of the second predetermined range,
wherein the identifiers in the first and second predetermined ranges are associated with CSI-RS ports with first and second polarization states, respectively.

* * * * *

UNITED STATES PATENT AND TRADEMARK OFFICE
CERTIFICATE OF CORRECTION

PATENT NO. : 10,263,746 B2  
APPLICATION NO. : 15/032648  
DATED : April 16, 2019  
INVENTOR(S) : Gao et al.

Page 1 of 2

It is certified that error appears in the above-identified patent and that said Letters Patent is hereby corrected as shown below:

On the Title Page

On Page 2, in Item (56), under "OTHER PUBLICATIONS", in Column 1, Line 1, delete "CSI_RS" and insert -- CSI-RS --, therefor.

On Page 2, in Item (56), under "OTHER PUBLICATIONS", in Column 1, Line 7, delete "CSI-Rs" and insert -- CSI-RS --, therefor.

In the Drawings

Figure 6A:
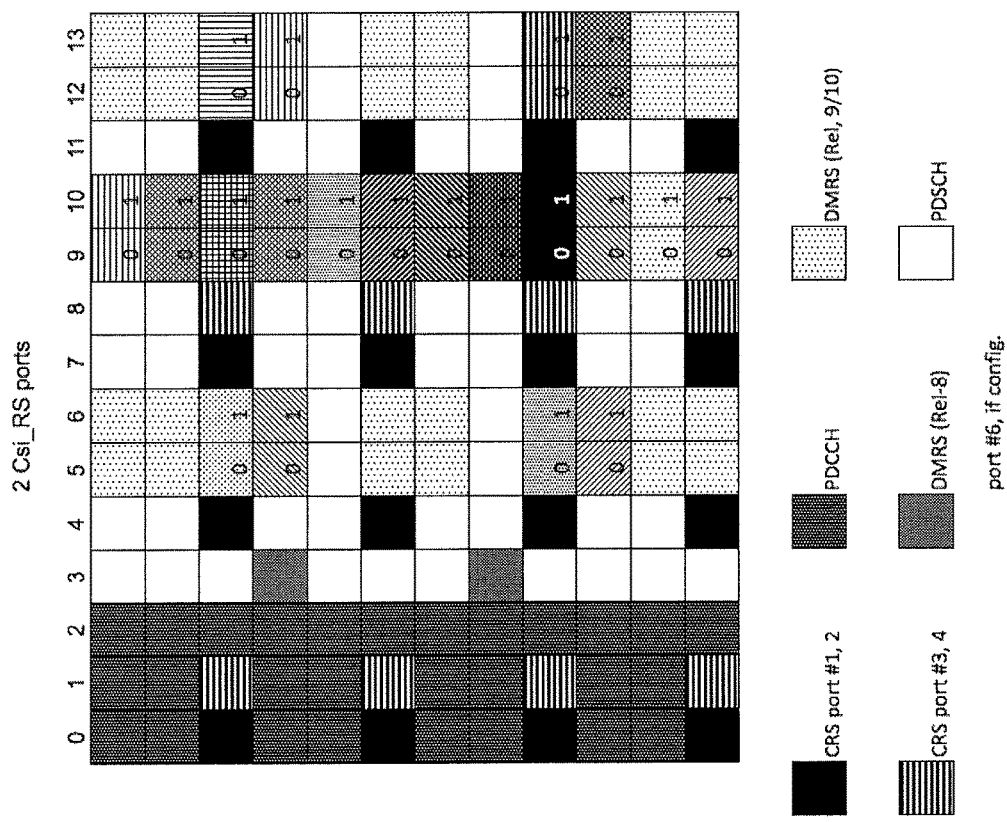
FIGS. 6A-6C illustrate resource element grids.
Figure 6B:
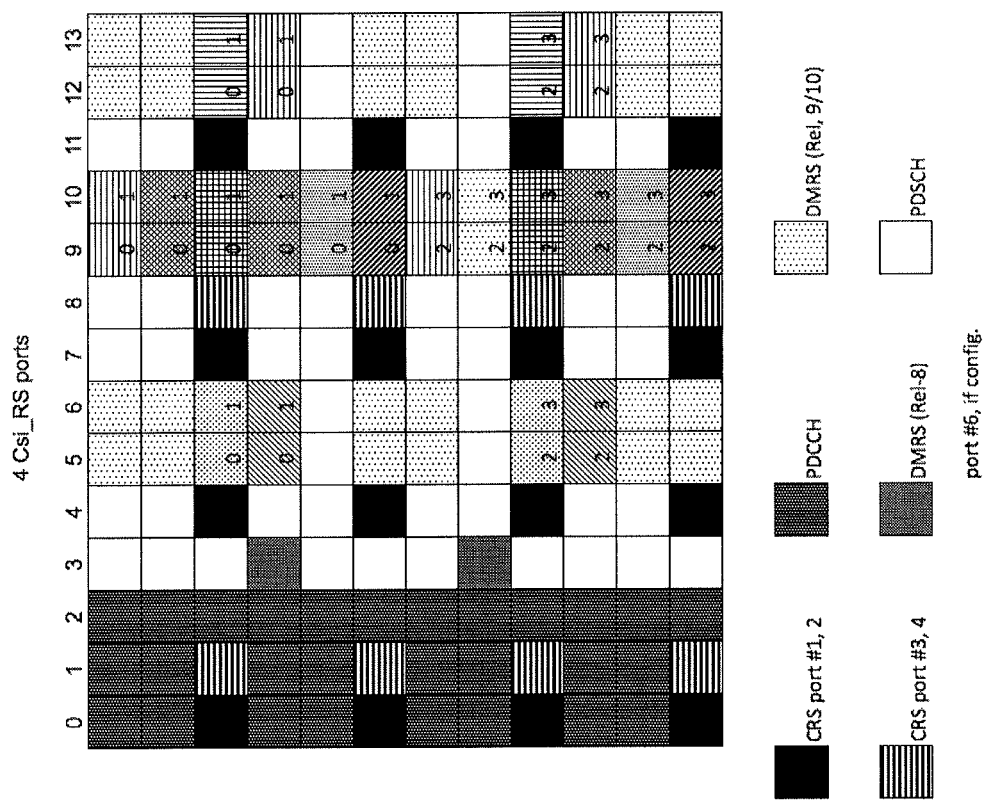
Figure 6C:
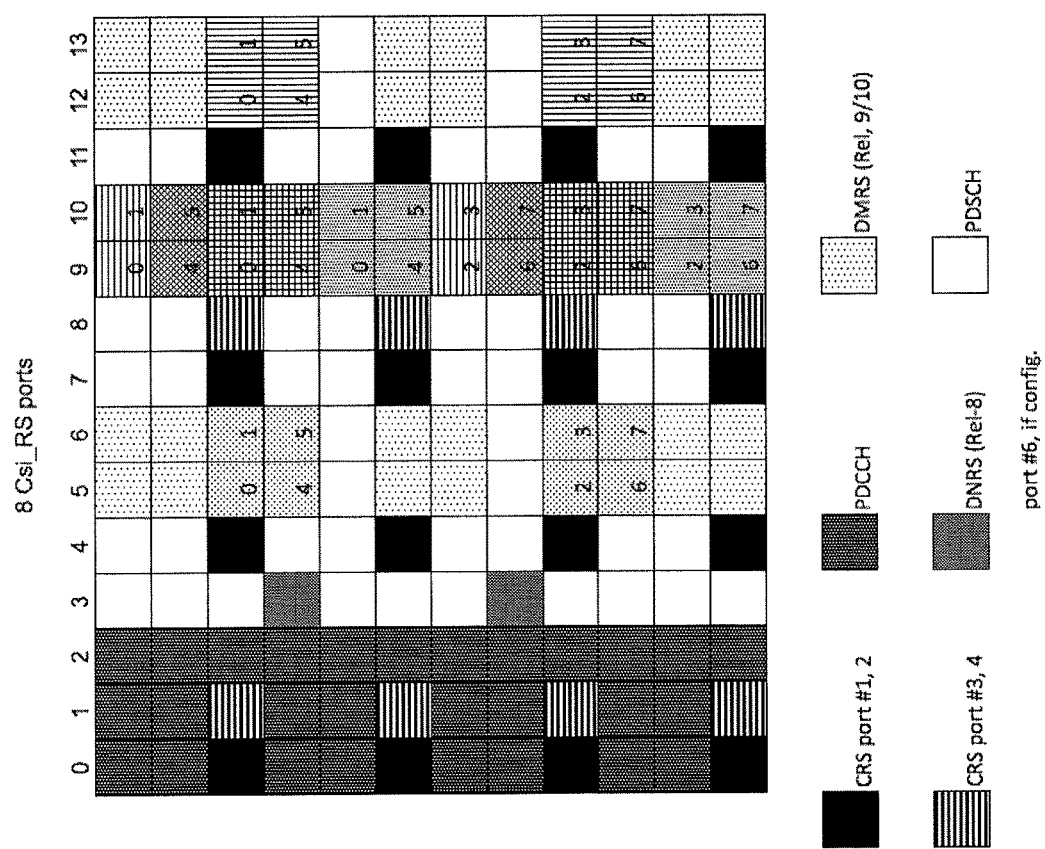
Figure 8:
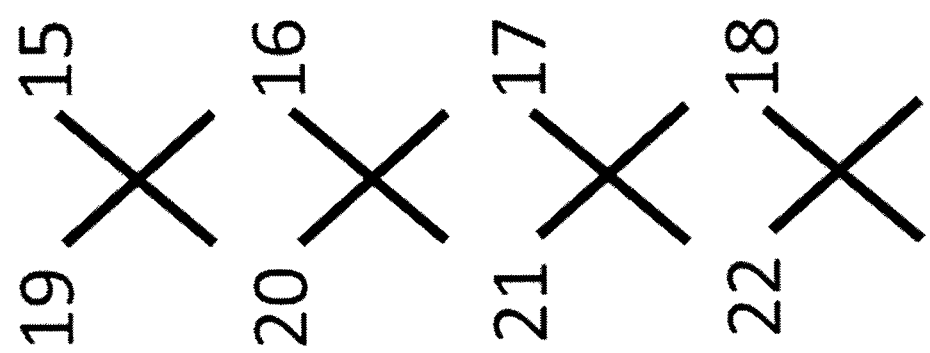
FIG. 8 illustrates the port numbering for P=8 antenna ports.

In Fig. 6C, Sheet 8 of 24, delete "DNRS" and insert -- DMRS --, therefor.

In Fig. 12, Sheet 14 of 24, delete "8-pport" and insert -- 8-port --, therefor.

In Fig. 15, Sheet 17 of 24, delete "8-pport" and insert -- 8-port --, therefor.

In the Specification

In Column 4, Line 38, delete "$w_{1'}$." and insert -- $w_{1''}$. --, therefor.

In Column 7, Line 64, delete "$m=N_v \cdot k+1$" and insert -- $m=N_v \cdot k+l$ --, therefor.

In Column 8, Line 55, delete "α" and insert -- a --, therefor.

In Column 9, Line 15, delete "CSI_RS" and insert -- CSI-RS --, therefor.

In Column 11, Line 4, delete "associated the" and insert -- associated with the --, therefor.

In Column 16, Line 34, delete "CSI-RS ports," and insert -- N CSI-RS ports, --, therefor.

Signed and Sealed this  
Twenty-second Day of October, 2019

Andrei Iancu  
*Director of the United States Patent and Trademark Office*

CERTIFICATE OF CORRECTION (continued)
U.S. Pat. No. 10,263,746 B2

In Column 28, Line 43, delete "associated the" and insert -- associated with the --, therefor.

In Column 30, Line 56, delete "associated the" and insert -- associated with the --, therefor.

In the Claims

In Column 31, Line 48, in Claim 1, delete "subset Channel" and insert -- subset of Channel --, therefor.

In Column 32, Line 6, in Claim 1, delete "Q<P," and insert -- Q≤P, --, therefor.

In Column 32, Lines 40-44, in Claim 5, delete "
$$p = \begin{cases} r + \frac{N}{2}k & r = 15, 16, \ldots, 14 + \frac{N}{2} \\ r + \frac{N}{2}(k + K - 1) & r = 15 + \frac{N}{2}, \ldots, 14 + N \end{cases}$$
" and insert --
$$p = \begin{cases} r + \frac{N}{2}k & r = 15, 16, \ldots, 14 + \frac{N}{2} \\ r + \frac{N}{2}(k + K - 1) & r = 15 + \frac{N}{2}, \ldots, 14 + N \end{cases} \quad (\text{Eq. 1})$$
--, therefor.

In Column 32, Line 45, in Claim 5, delete "K_" and insert -- K --, therefor.

In Column 33, Lines 36-38, in Claim 12, delete "
$$p' = \begin{cases} p' & q = 0; \\ p - \frac{KN - Q}{2}, & q = 1. \end{cases}$$
" and insert --
$$p' = \begin{cases} p, & q = 0; \\ p - \frac{KN - Q}{2}, & q = 1, \end{cases}$$
--, therefor.

In Column 36, Line 9, in Claim 23, delete "Q<P," and insert -- Q≤P, --, therefor.

In Column 36, Line 31, in Claim 24, delete "processors," and insert -- processors --, therefor.